Figure 1:
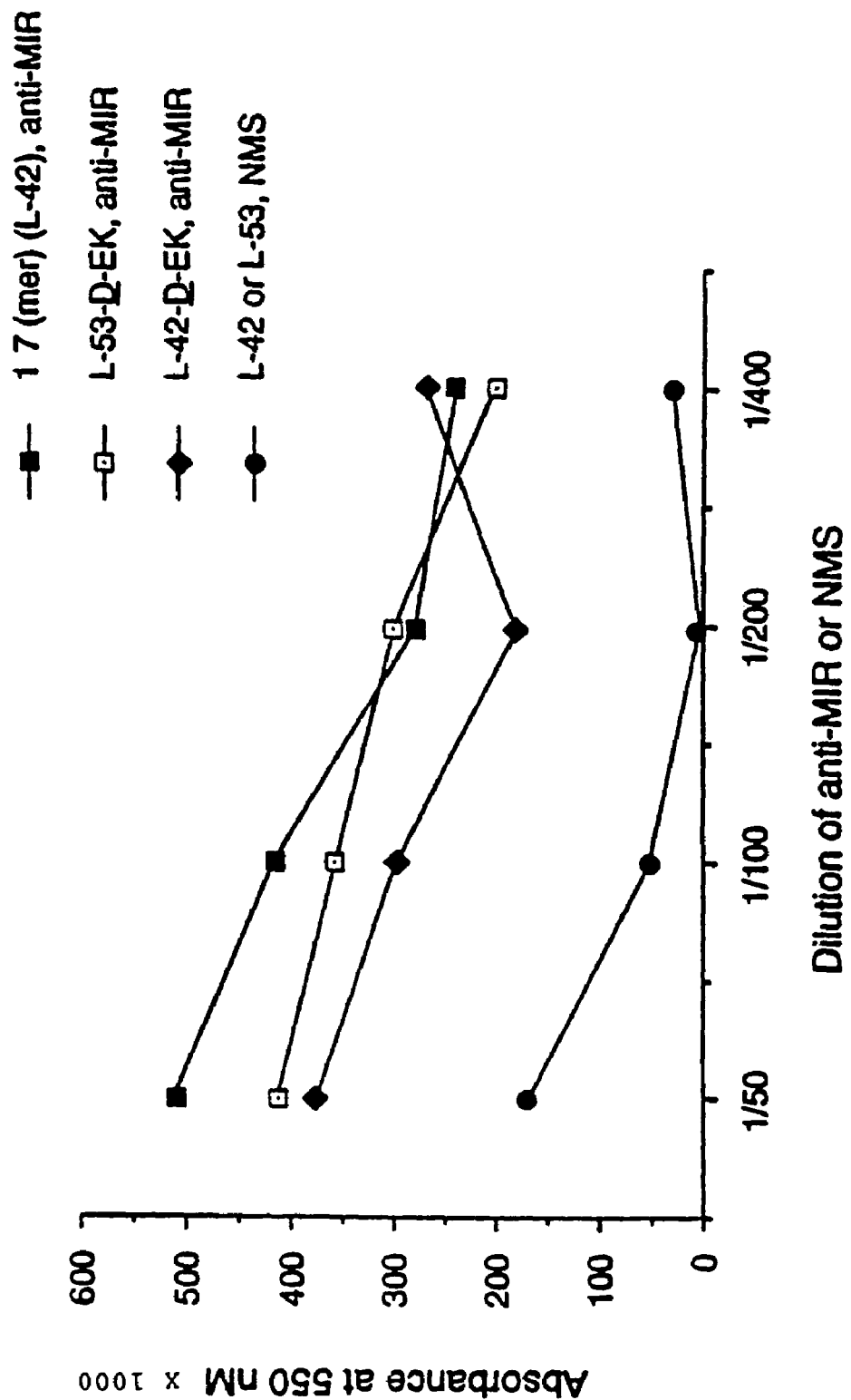

US007138244B2

(12) United States Patent
Barstad et al.

(10) Patent No.: US 7,138,244 B2
(45) Date of Patent: *Nov. 21, 2006

(54) COMPOSITION FOR INDUCING HUMORAL ANERGY TO AN IMMUNOGEN COMPRISING A T CELL EPITOPE-DEFICIENT ANALOG OF THE IMMUNOGEN CONJUGATED TO A NONIMMUNOGENIC VALENCY PLATFORM MOLECULE

(75) Inventors: Paul A. Barstad, Bountiful, UT (US); Gilbert M. Iverson, Del Mar, CA (US)

(73) Assignee: La Jolla Pharmaceutical Company, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/957,198

(22) Filed: Oct. 1, 2004

(65) Prior Publication Data

US 2005/0170436 A1 Aug. 4, 2005

Related U.S. Application Data

(60) Division of application No. 10/081,076, filed on Feb. 20, 2002, which is a continuation of application No. 09/563,167, filed on May 2, 2000, now abandoned, which is a continuation of application No. 08/118,055, filed on Sep. 8, 1993, now Pat. No. 6,060,056, which is a continuation-in-part of application No. 07/652,648, filed on Feb. 8, 1991, now Pat. No. 5,268,454.

(51) Int. Cl.
*G01N 33/53* (2006.01)

(52) U.S. Cl. ....................... 435/7.1; 435/7.2; 435/7.21; 435/7.24; 435/7.25; 436/543; 530/333; 530/402

(58) Field of Classification Search .......... 435/7.1–7.4; 436/543; 530/333, 402
See application file for complete search history.

(56) References Cited

U.S. PATENT DOCUMENTS

| | | | |
|---|---|---|---|
| 4,191,668 | A | 3/1980 | Katz |
| 4,220,565 | A | 9/1980 | Katz |
| 4,388,441 | A | 6/1983 | Katz |
| 4,430,260 | A | 2/1984 | Lee et al. |
| 4,599,231 | A | 7/1986 | Milich et al. |
| 4,650,625 | A | 3/1987 | Pentlow |
| 4,650,675 | A | 3/1987 | Borel et al. |
| 4,722,899 | A | 2/1988 | Hamaoka |
| 4,803,070 | A | 2/1989 | Cantrell et al. |

(Continued)

FOREIGN PATENT DOCUMENTS

WO WO 91/10426 7/1991

(Continued)

OTHER PUBLICATIONS

Abbas, A. et al. eds. (1991). "Lymphocyte Specificity and Activation," Chapter 6 *In Cellular and Molecular Immunology*. W.B. Saunders Company: Philadelphia, pp. 116-124.

(Continued)

*Primary Examiner*—David Saunders
(74) *Attorney, Agent, or Firm*—Morrison & Foerster LLP

(57) ABSTRACT

Conjugates of nonimmunogenic valency platform molecules and analogs of immunogens that possess the specific B cell binding ability of the immunogen but lack T cell epitopes and which, when introduced into individuals, induce humoral anergy to the immunogen are disclosed. Accordingly, these conjugates are useful for treating antibody-mediated pathologies that are caused by foreign or self immunogens.

17 Claims, 11 Drawing Sheets

U.S. PATENT DOCUMENTS

| | | | |
|---|---|---|---|
| 4,863,740 | A | 9/1989 | Kissel et al. |
| 4,886,782 | A | 12/1989 | Good et al. |
| 4,925,787 | A | 5/1990 | Tanihara et al. |
| 4,950,469 | A | 8/1990 | Katz |
| 4,950,713 | A | 8/1990 | Katz |
| 5,017,648 | A | 5/1991 | Katz |
| 5,102,663 | A | 4/1992 | Livingston et al. |
| 5,126,131 | A | 6/1992 | Dintzis et al. |
| 5,162,515 | A | 11/1992 | Conrad et al. |
| 5,177,188 | A * | 1/1993 | Ginsberg et al. ............ 530/324 |
| 5,268,454 | A | 12/1993 | Barstad et al. |
| 5,276,013 | A | 1/1994 | Conrad et al. |
| 5,529,922 | A | 6/1996 | Chapman et al. |
| 5,552,391 | A | 9/1996 | Coutts et al. |
| 5,606,047 | A | 2/1997 | Coutts et al. |
| 5,633,395 | A | 5/1997 | Coutts et al. |
| 5,736,146 | A | 4/1998 | Cohen et al. |
| 5,874,409 | A | 2/1999 | Victoria et al. |
| 6,022,544 | A | 2/2000 | Dintzis et al. |
| 6,060,056 | A | 5/2000 | Coutts et al. |
| 6,207,160 | B1 | 3/2001 | Victoria et al. |
| 6,340,460 | B1 * | 1/2002 | Dintzis et al. ........... 424/184.1 |
| 6,410,775 | B1 | 6/2002 | Victoria et al. |
| 6,858,210 | B1 | 2/2005 | Marquis et al. |
| 2002/0082400 | A1 | 6/2002 | Coutts et al. |
| 2002/0107389 | A1 | 8/2002 | Coutts et al. |
| 2003/0103990 | A1 | 6/2003 | Coutts et al. |
| 2003/0162953 | A1 | 8/2003 | Coutts et al. |
| 2005/0004351 | A1 | 1/2005 | Marquis et al. |
| 2005/0026856 | A1 | 2/2005 | Coutts et al. |
| 2005/0031635 | A1 | 2/2005 | Coutts et al. |

FOREIGN PATENT DOCUMENTS

| | | |
|---|---|---|
| WO | WO 91/12816 | 9/1991 |
| WO | WO 92/11029 | 7/1992 |
| WO | WO 92/11030 | 7/1992 |
| WO | WO 92/13558 | 8/1992 |
| WO | WO 93/02093 | 2/1993 |

OTHER PUBLICATIONS

Ada, G.L. (1987). "The Generation of Cellular vs. Humoral Immunity," Chapter 3 in *Synthetic Vaccines*. Arnon, R., ed, CRC Press, Boca Raton, FL, pp. 25-37.

Alemany et al. (1987). "Phospho-dephospho-control by Insulin is Mimicked by a Phospho-oligosaccharide in Adipocytes," *Nature* 330:77-79.

Alvarez et al. (1991). "Transport in Isolated Rat Hepatocytes of the Phospho-oligosaccharide that Mimics Insulin Action," *Biochem J.* 274:369-374.

Bach, J.F and J.P.Viard. (1990). "Hypothesis: Systemic Lupus Erythematosus as a Disease Secondary to Polyclonal Lymphocyte Activation," *Clin. Exp. Rheumatol.* 8 (Suppl. 5):57-64.

Barstad et al. U.S. Appl. No. 10/957,198, filed on Oct. 1, 2004.

Bennett et al. (1992). "Idiotypic Mimicry of a Cell Surface DNA Receptor: Evidence for Anti-DNA Antibodies Being a Subset of Anti-DNA Receptor Antibodies," *Clin. Exp. Immunol.* 90:428-433.

Bock et al. (1992). "Selection of Single-Stranded DNA Molecules that Bind and Inhibit Human Thrombin," *Nature* 355:564-566.

Bootsma et al. (1995). "Prevention of Relapses in Systemic Lupus Erythematosus," *Lancet* 345:1595-1599.

Borel, H. and T. Borel. (1990). "A Novel Technique to Link Either Proteins or Peptides to Gammaglobulin to Construct Tolerogens," *Journal of Immunological Methods* 126:159-168.

Borel, Y and H. Borel. (1988). "Oligonucleotide Linked to Human Gammaglobulin Specifically Diminishes Anti-DNA Antibody Formation in Cultured Lymphoid Cells from Patients with Systemic Lupus Erythematosus," *J. Clin. Invest.* 82: 1901-1907.

Bradley, L.M. et al., (1980) "6.4 Antigen-Induced T Cell Proliferative Responses" *Selected Methods In Cellular Immunology*, Mishell, B.B. and S.M. Shiigi, eds., pp. 164-166.

Burke, J.M. and A. Berzal-Hemanz. (1993). "*In Vitro* Selection and Evolution of RNA: Applications for Catalytic RNA, Molecular Recognition, and Drug Discovery," *FASEB J.* 7:106-112.

Butterfield et al. (1981). "Immunotherapy with Short Ragweed Fraction A: D-glutamic Acid: D-lysine Polymer in Ragweed Hay Fever," *J. Allergy Clin. Immun.* 67:272-278.

Chiller, J.M and W.O. Weigle. (1975). "Biography of a Tolerant State: Cellular Parameters of the Unresponsive State Induced in Adult Mice to Human Gamma Globulin," *J. Reticuloendothelial Soc.* 17(3):180-186.

Coulson, E.J. and H. Stevens. (1961). "Some Observations on the Immunochemistry of Dextrans" *J. Immunol.* 86: 241-252.

Cwirla et al. (1990). "Peptides on Phage: A Vast Library of Peptides for Identifying Ligands," *PNAS USA* 87:6378-6382.

De Franco, A. (1989). "Tolerance: A Second Mechanism," *Nature* 342:340-341.

Devlin et al. (1990). "Random Peptide Libraries: A Source of Specific Protein Binding Molecules," *Science* 249:404-406.

Diamond et al. (1992). "The Role of Somatic Mutation in the Pathogenic Anti-DNA Response," *Ann. Rev. Immunol.* 10:731-757.

Diamond, B. and M.D. Scharff. (1984). "Somatic Mutation of the T15 Heavy Chain Gives Rise to an Antibody with Autoantibody Specificity," *Proc. Natl. Acad. Sci. USA* 81:5841-5844.

Diner et al. (1979). "Carboxymethyl Cellulose, a Nonimmunogenic Hapten Carrier with Tolerogenic Properties," *J. Immunol.* 122(5):1886-1891.

Dintzis et al. (1976). "Molecular Determinants of Immunogenicity: the Immunon Model of Immune Response," *Proc. Natl. Acad. Sci. USA* 73(10):3671-3675.

Dintzis et al. (1982). "Specific Cellular Stimulation in the Primary Immune Response: Experimental Test of a Quantized Model," *PNAS USA* 79:884-888.

Dintzis et al. (1983). "Studies on the Immunogenicity and Tolerogenicity of T-Independent Antigens,"*J. Immunol.* 131(5):2196-2203.

Dintzis et al. (1985). "Inhibition of Anti-DNP Antibody Formation by High Doses of DNP-Polyacrylamide Molecules: Effects of Hapten Density and Hapten Valence," *Journal of Immunology* 135(1):423-427.

Dintzis et al. (1989). "The Immunogenicity of Soluble Haptenated Polymers is Determined by Molecular Mass and Hapten Valence," *J. Immunol.* 143(4):1239-1244.

Etlinger, H. and M. Chiller. (1977). "Induction of Tolerance in Athymic Mice with an Antigen Which is Highly Immunogenic in Euthymic Mice," *Cell. immunol.* 33:297-308.

Finkelman, F.D. (1995). "Cross-linking of Membrane Immunoglobin D, in the Absence of T Cell Help, Kills Mature B Cells *In Vivo*," *J. Exp. Med.* 181:515-525.

Francis et al. (1988). "Peptides With Added T-cell Epitopes Can Overcome Genetic Restriction of the Immune Response," *Vaccines 88*. Ginsberg, H., et al., eds., Cold Spring Harbor Laboratory, pp. 1-7.

Fulcher et al. (1994). "Whither the Anergic B-Cell?" *Autoimmunity* 19:135-140.

Garrido, M.J. and C. Moreno. (1979). "The Use of Hapten-Polysaccharide Conjugates for the Induction of B-Cell Tolerance Involving IgE Responses," *Int. Archs. Allergy Appl: Immunol.* 60:161-168.

Garvey et al. eds. (1977). *Methods In Immunology*, 3rd. ed., pp. 301-302.

Geysen et al. (1986). "The Delineation of Peptides Able to Mimic Assembled Epitopes," *Synthetic Peptides as Antigens*, Ciba Symposium 119:130-149.

Golan, D.T and Y. Borel. (1971). "Nonantigenicity and Immunologic Tolerance: the Role of the Carrier in the Induction of Tolerance to the Hapten," *J. Exp Med.* 134:1046-1061.

Goodnow, C.C. (1989). "Induction of Self-Tolerance in Mature Peripheral B Lymphocytes," *Nature* 342:385-391.

Green, D.R. (1983). "Immunoregulatory T-cell Pathways," *Ann.Rev. Immunol.* 1:439-463.

Habicht, G.S. (1973). "Methods for the Study of the Cellular Basis of Immunologic Tolerance", Chapter 6 *in Immune Response at the Cellular Level*. Zacharia, T. P., ed., Marcel Dekker, Inc., New York, NY, pp. 141-160.

Hartley et al. (1993). "Elimination of Self-Reactive B Lymphocyte Proceeds in Two Stages: Arrested Develoment and Cell Death," *Cell* 72:325-335.

Hefeneider et al. (1993). "Immunization of BALB/c Mice with a Monoclonal Anti-DNA Antibody Induces an Anti-idiotypic Antibody Reactive with a Cell-surface DNA Binding Protein," *Autoimmunity* 15:187-194.

Heidenreich et al. (1994). "T Cell-dependent Activity of Ganglioside GM1-specific B Cells in Guillain-Barré Syndrome and Multifocal Motor Neuropathy *in vitro*," *J. Neuroimmunol.* 49:97-108.

Holford-Strevens et al. (1982). "Suppression of IgE Antibody Production in Sensitized Mice and Rats by Tolerogenic Conjugates of Synthetic Hydrophilic Polymers with Antigen or Hapten: Effects on Antigen-induced Histamine Release from Peritoneal Mast Cells," *Int. Archs. Allergy Appl. Immunol.* 67:109-116.

Hudson et al. (1986). "Cloning and Expression of a Viral Phosphoprotein:Structure Suggests Vesicular Stomatitis Virus NS May Function by Mimicking an RNA Template," *J. Gen. Virol.* 67:1571-1579.

Isenberg et al. (1994). "The Origin, Sequence, Structure, and Consequences of Developing Anti-DNA Antibodies, A Human Perspective," *Arthritis Rheum.* 37:169-180.

Isenberg, D.A. and Y. Shoenfeld. (1988). "An Analysis of Autoimmunity Through Studies of DNA Antibody Idiotypes," *Autoimmunity* 1:67-75.

Iverson, G.M. (1986). "Assay for *In Vivo* Adoptive Immune Response" Chapter 67 *In Handbook of Experimental Immunology* 2: 67.1-67.8.

Jacob, L. and J.P. Viard. (1992). "Anti-DNA Antibodies and Their Relationships with Anti-histone and Anti-nucleosome Specificities," *Eur. J. Med.* 1:425-431.

Jacobs et al. (1997). "Humoral Immune Response Against *Campylobacter jejuni* Lipopolysaccharides in Guillain-Barré and Miller Fisher Syndrome," *J. Neuroimmunol.* 79:62-68.

Janeway, C.A., Jr. and P. Travers. eds. (1994). *Immunobiology: The Immune System in Health and Disease*. Garland, London (Table of Contents).

Johnson et al. (1996). "Prolonged and Preferential Production of Polymeric Immunoglobulin A in Response to *Streptococcus pneumoniae* Capsular Polysaccharides," *Infection and Immunity* 64:4339-4344.

Kato et al. (1990). "Protection of Mice Against the Lethal Toxicity of a Lipopolysaccharide (LPS) by Immunization with Anti-Idiotype Antibody to a Monoclonal Antibody to Lipid A from *Eikenella Corrodens* LPS," *Infection and Immunity* 58(2);416-420.

Katz et al. (1971). "Carrier Function in Anti-hapten Antibody Responses. IV. Experimental Conditions for the Induction of Hapten-specific Tolerance or for the Stimulation of Anti-hapten Anamnestic Responses by "Nonimmunogenic" Hapten-polypeptide Conjugates," *J. Exp. Med.* 134(1):201-223.

Kaur et al. (1997). "Topological Analysis of the functional mimicry between a peptide and a carbohydrate moiety," *J. Biol. Chem.* 272(9):5539-5543.

Kieber-Emmons et al. (1997). "Peptide Mimicry of Adenocarcinoma-Associated Carbohydrate Antigens," *Hybridoma* 16(1):3-10.

Kronborg et al. (1993). "Specific IgG2 Antibodies to *Pseudomonas aeruginosa* lipid A and Lipopolysaccharide are Early Markers of Chronic Infection in Patients with Cystic Fibrosis," *Infection* 21:297-302.

Lal et al. (1991). "A Synthetic Peptide Elicits Antibodies Reactive with the External Glycoprotein of Human T Cell Lymphotropic Virus Type 1," *J. Gen. Virol.* 72:2321-2324.

Lee et al. (1993). "Abrogation of the Antibenzylpenicilloyl (BPO) IgE Response with BPO-polyvinyl Alcohol Conjugates," *Int. Archs Allergy Appl. Immunol.* 63:1-13.

Lee, W.Y. and A.H. Sehon. (1987). "Abrogation of Reaginic Antibodies with Modified Allergens," *Nature* 267:618-619.

Lees et al. (1996). "Activation of Soluble Polysaccharides With 1-cyano-4-dimethylaminopyridinium tetrafluoroborate for Use in Protein-polysaccharide Conjugate Vaccines and Immunological Reagents," *Vaccine* 14:190-198.

Liu et al. (1979). "Immunologic Tolerance to Allergenic Protein Determinants: Properties of Tolerance Induced in Mice Treated with Conjugated of Protein and a Synthetic Copolymer of $_D$-glutamic Acid and $_D$-lysine ($_D$GL)," *J. Immun.* 123:2456-2464.

Livneh, A. (1993). "Anti-DNA Antibodies Secreted by Peripheral B Cells of Lupus Patients Have Both Normal and Lupus-specific Features," *Clin. Immunol. Immunopathol.* 68:68-73.

Loizou et al. (1992). "Immunoglobulin Class and IgC Subclass Distribution of Anticardiolipin Antibodies in Patients with Systemic Lupus Erythematosus and Associated Disorders," *Clin. Exp. Immunol* 90:434-439.

Macaya et al. (1993). "Thrombin-binding DNA Aptamer Forms a Unimolecular Quadruplex Structure in Solution," *Proc. Natl. Acad. Sci. USA* 90:3745-3749.

Mandrell, R.E. and M.A. Apicella. (1993). "Lipo-oligosaccharides (LOS) of Mucosal Pathogens: Molecular Mimicry and Host-Modification of LOS," *Immunobiol.* 187:382-402.

Mitchell et al. (1972). "Inhibition of Secondary Anti-hapten Responses with the Hapten Conjugated to Type 3 Pneumococcal Polysaccharide," *Eur. J. Immunol.* 2:460-467.

Morimoto et al. (1987). "A Defect of Immunoregulatory T Cell Subsets in Systemic Lupus Erythematosus Patients Demonstrated with Anti-2H4 Antibody," *J. Clin. Invest.* 79:762-768.

Mozes, E. and S. Mendlovic. (1990). "The Role of Anti-DNA idiotype Antibodies in Systemic Lupus Erythematosus," *Critical Reviews in Immunology* 10(4):329-345.

Norman, P.S. (1984). "Immunologic Responses to Conjugates of Antigen E in Patients with Ragweed Hay Fever," *J. Allergy Clin. Immunol.* 73(6):782-789.

Norvell et al. (1995). "Engagement of the Antigen-receptor on Immature Murine B Lymphocytes Results in Death by Apoptosis," *J. Immunol.* 154: 4404-4413.

Nossal, G.J.V. (1989a). "Immunologic Tolerance" Chapter 19 *In Fundamental Immunology*. W.E. Paul, ed., Raven Press, NY, pp. 571-586, especially pp. 577-589.

Nossal, G.J.V. (1989b). "Immunologic Tolerance: Collaboration Between Antigen and Lyphokines," *Science* 245:147-153.

Novak, Z. (1992) "Evidence for Immunodominance Between Closely Related Epitopes in the Selection of T Cell Repertoire Hierarchy of T Cell Epitopes in a Repeating Sequence," *Molec. Immunol.* 29(12):1467-1476.

Olsson, L. "Molecular Mimicry of Carbohydrate and Protein Structures by Hybridoma Antibodies," *Bio Essays* 7(3): 116-119.

Pisetsky, D.S. (1993). "Autoantibodies and Their Significance," *Curr. Opin. Rheumatol.* 5:549-556.

Puccetti et al. (1990). "Human and Murine Anti-DNA Antibodies Induce the Production of Anti-idiotypic Antibodies With Autoantigen-binding Properties (epibodies) Through Immune-network Interactions," *J. Immunol.* 145:4229-4237.

Radic, M.Z. and M. Weigert. (1994). "Genetic and Structural Evidence for Antigen Selection of Anti-DNA Antibodies," *Ann. Rev. Immunol.* 12:487-520.

Rahman, M.A. and D.A. Isenberg. (1994). "Autoantibodies in Systemic Lupus Erythematosus," *Curr. Opin. Rheumatol.* 6:468-473.

Reeves et al. (1994). "Systemic Lupus Erythematosus. Antibodies to DNA, DNA-binding Proteins, and Histones," *Rheum. Dis. Clin. North Am.* 20:1-28.

Renschler, M.F. (1994). "Synthetic Peptide Ligands of the Antigen Binding Receptor Induce Prgrammed Cell Death in a Human B-cell Lymphoma," *PNAS* 91:3623-3627.

Rieben et al. (1992). "Naturally Occurring ABO Antibodies: Long-term Stable, Individually Distinct Anti-A IgG Spectrotypes," *Eur. J. Immunol.* 22:2129-2133.

Rochu et al. (1990). "ABO-blood-group-related Idiotypic Network: Mimicry of Oligosaccharide Epitope by Rabbit Antiidiotypic Antibodies to Murine Monoclonal Anti-A Antibody," *Res. Immunol.* 141:373-387.

Rombach et al. (1993). "Induction of an Anti-Fab, Anti-DNA and Anti-RNA Polymerase I Autoantibody Response Network in Rabbits Immunized with SLE Anti-DNA Antibody," *Clin. Exp. Immunol.* 94:466-472.

Rose et al. eds. (1992). *Manual of Clinical Immunology* 4th ed., American Society for Microbiology, Washington, D.C., pp. 2:7-9.

Rozdzinski et al. (1993). "Antiinflammatory Effects in Experimental Meningitis of Prokaryotic Peptides that Mimic Selectins," *J. Infect. Diseases* 168:1422-1428.

Ruffatti et al. (1990). "Anti-double-stranded DNA Antibodies in the Healthy Elderly: Prevalence and Characteristics," *J. Clin. Immunol.* 10:300-303.

Sacks et al. (1985). "Molecular Mimicry of a Carbohydrate Epitope on a Major Surface Glycoprotein of *Trypanosoma cruzi* by Using Anti-idiotypic Antibodies," *J. Immunol.* 135(6):4155-4159.

Sasaki et al. (1982). "Induction of Immunological Tolerance to Single-Stranded and Double-Stranded DNA," *Scand. J. Immun.* 16:191-200.

Schreiber et al. (1991). "Anti-idiotype-induced, Lipopolysaccharide-specific Antibody Response to *Pseudomonas aeruginosa*," *J. Immunol.* 146:188-193.

Schumacher et al. (1996). "Fetal Transfusion for Red Blood Cell Alloimmunization in Pregnancy," *Obstet. and Gynecol.* 88(1):137-150.

Scott, J. and G. Smith. (1990) "Searching for Peptide Ligands with an Epitope Library," *Science* 249:386-390.

Sehon, A.H. (1982). "Suppression of Iae Antibody Responses with Tolerogenic Conjugates of Allergens and Haptens," *Prog. Allergy* 32:161-202.

Sehon, A.H. (1988). "Modulation of Antibody Responses by Conjugates of Antigens with Monomethoxypolyethylene Glycol," *Adv. Exp. Med. biol.* 251:341-351.

Sellers, J.R. "Polarity and Velocity of Sliding Filaments: Controls of Direction by Actin and of Speed by Myosin," *Science* 249:406-408.

Shoenfeld, Y. and E. Mozes. (1991). "Pathogenic Anti-DNA Idiotype (16/6 Id) in Systemic Lupus Erythematosus," *Rheumatol. Int.* 11:91-93.

Silva, D.J. (1994). "Use of Triethylene Glycol to Mimic Oligosaccharides: Design and Synthesis of a Ligand Based on Chromomycin $A_3$," *Bioorganic and Medicinal Chem.* 2(11):1251-1259.

Singh et al. (1995). "T Cell Determinants from Autoantibodies to DNA can Upregulate Autoimmunity in Murine Systemic Lupus Erythematosus," *J. Exp. Med.* 181:2017-2027.

Sontheimer et al. (1992). "Antinuclear Antibodies: Clinical Correlations and Biological Significance," *Adv. Dermatol.* 7:3-52.

Steinberg, A.D. (1991). "NIH Conference. Systemic Lupus Erythematosus," *Ann. Intern. Med.* 115:548-559.

Stemme et al. (1995). "T Lymphocytes from Human Atherosclerotic Plaques Recognize Oxidised Low Density Lipoprotein," *Proc. Natl. Acad. Sci. USA* 92:3893-3897.

Stott et al. (1988). "Expression of Anti-DNA Clonotypes and the Role of Helper T-lymphocytes During the Autoimmune Response in Mice Tolerant to Alloantigens," *Autoimmunity* 1:253-266.

Stroud, R.M. and J. Finer-Moore. (1985). "Acetylcholine Receptor Structure, Function, and Evolution," *Ann. Rev. Cell Biol.* 1:317-351.

Sumikawa et al. (1982). "The Molecular Cloning and Characterisation of cDNA Coding for the a Subunit of the Acetylcholine Receptor," *Nucl. Acids Res.* 10(19):5809-5822.

Sutherland, A.D. (1993). "An Experimental Anti-idiotype Vaccine Mimicking Lipopolysaccharide Gives Protection Against *Pasteurella multocida* Type A Infection in Mice,"*FEMS Immunol. and Medical Microbiol.* 7:105-110.

Tanasescu et al. (1988). "HBsAg Positive Secondary Autoimmune Active Chronic Hepatitis. Immunogenetic Aspects," *Rev. Roum. Med.—Med. Int.* 26(1):53-66.

Ter Borg et al. (1991). "Rises in Anti-double Stranded DNA Antibody Levels Prior to Exacerbations of Systemic Lupus Erythematosus are Not Merely Due to Polyclonal B Cell Activation," *Clin. Immunol and Immunopathol.* 59:117-128.

Thorpe et al. (1984). "Blockade of the Galactose-Binding Sites of Ricin by its Linkage to Antibody: Specific Cytotoxic Effects of the Conjugates," *European Journal of Biochemistry* 140:63-71.

Victoria et al. U.S. Appl. No. 10/846,079, filed on May 13, 2004.

Wang et al. (1991). "Induction of Anti-progesterone Immunity and Pregnancy Blocking by Anti-progesterone Anti-idiotypes. Variable Efficacy of Polyclonal Ab2 Antibodies Directed against a Panel of Closely Related Ab1 Antibodies," *Immunology* 73:348-355.

Watanabe et al. (1991). "Detection of Immunoglobulin G Antibodies to Cholesterol in Antisera to Mycoplasmas," *Infection and Immunity* 59:2200-2202.

Watanabe, M.R. and M.A., Aldo-Benson. (1983). "Specific Suppression of Hybridoma Immunoglobulin Secretion by Hapten-conjugated Mouse IgG: a Model of B Cell Tolerance," *Cellular Immunol.* 79:345-357.

Watanabe-Kukunaga, R. (1992). "Lymphoproliferative Disorder in Mice Explained by Defects in Fas Antigen that Mediates Apoptosis," *Nature* 356:314-317.

Weltman et al. (1983). "N-Succinimidyl (4-Iodoacetyl) Aminobenzoate: A New Heterobifunctional Crosslinker," *Biotechniques* 1:148-152.

Wilkinson et al. (1987). "Tolerance Induction in Mice by Conjugates of Monoclonal Immunoglobulins and Monomethoxypolyethylene Glycol," *J. Immunol.* 139:326-331.

Willison, H.J. and J. Veitch. (1994). "Immunoglobulin Subclass Distribution and Binding Characteristics of Anti-GQ1b Antibodies in Miller Fisher Syndrome," *J. Neuroimmunol.* 50:159-165.

Wünsch et al. (1991). "Fully Synthetic Immonogens," *Int. J. Peptide Res.* 37:90-102.

Zack et al. (1994). "Novel Structural Features of Autoantibodies in Murine Lupus: A Possible Superantigen Binding Site?," *Immunol. Cell Biol.* 72:513-520.

Zack et al. (1995). "DNA Mimics a Self-protein That May be a Target for Some Anti-DNA Antibodies in Systemic Lupus Erythematosus," *J. Immunol.* 154:1987-1994.

* cited by examiner

Melittin Peptide Conjugates

Melittin Conjugate # 1, R = H₂N-Trp-Ile-Lys-Arg-Lys-Arg-Gln-Gln-Lys-Cys-Gly-CO₂H Average n = approx. 74

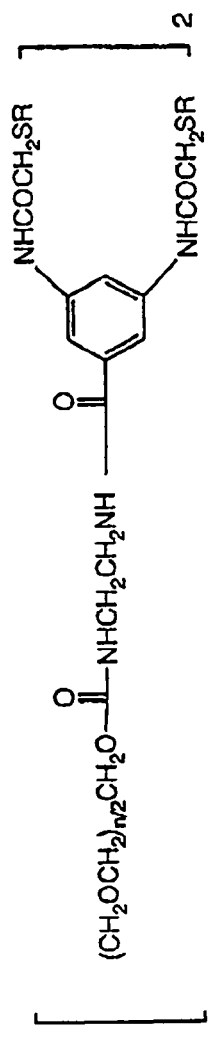

Melittin Conjugate # 2, R = H₂N-Cys-Trp-Ile-Lys-Arg-Lys-Arg-Gln-Gln-Lys-Cys-Gly-CO₂H
Melittin Conjugate # 3, R = H₂N-Trp-Ile-Lys-Arg-Lys-Arg-Gln-Gln-Lys-Cys-Gly-CO₂H
Melittin Conjugate # 4, R = H₂N-Cys-Ile-Ser-Trp-Ile-Lys-Arg-Lys-Arg-Gln-Gln-Lys-Gly-CO₂H
Melittin Conjugate # 5, R = (H₂N-Trp-Ile-Lys-Arg-Lys-Arg-Gln-Gln)₂-Lys-Cys-Gly-CO₂H Melittin peptides attached through sulfur atom on added cysteine, average n = approx. 74

FIGURE 11

COMPOSITION FOR INDUCING HUMORAL ANERGY TO AN IMMUNOGEN COMPRISING A T CELL EPITOPE-DEFICIENT ANALOG OF THE IMMUNOGEN CONJUGATED TO A NONIMMUNOGENIC VALENCY PLATFORM MOLECULE

RELATED APPLICATIONS

This application is a divisional of Ser. No. 10/081,076, filed Feb. 20, 2002, which is a continuation of Ser. No. 09/563,167, filed May 2, 2000, now abandoned, which is a continuation of Ser. No. 08/118,055, filed Sep. 8, 1993, now U.S. Pat. No. 6,060,056, which is a continuation-in-part of Ser. No. 07/652,648, filed Feb. 8, 1991, now U.S. Pat. No. 5,268,454, the disclosures of which are incorporated herein by reference.

TECHNICAL FIELD

This invention is in the field of immunology and concerns compositions and methods for inducing humoral anergy for the purpose of treating antibody-mediated pathologies. More specifically, the invention relates to conjugates of nonimmunogenic valency platform molecules and analogs of immunogens that lack T cell epitopes.

BACKGROUND OF THE INVENTION

In order to survive in a world of pathogenic or potentially pathogenic microorganisms, higher organisms have evolved immune systems which can specifically recognize virtually any foreign substance through its characteristic molecules. This recognition frequently results in the production of specific proteins called antibodies which bind only to the foreign substance which induced their synthesis, causing the elimination of the invading microorganism. Occasionally an animal's immune system makes antibodies which recognize some of its own molecules, generating an autoimmune state that may affect the animal's health adversely.

The induction of specific antibodies in response to an immunogen involves the interaction of multiple cell types, including thymus-derived lymphocytes (T cells), macrophages, and bone marrow-derived lymphocytes (B cells). This is in contrast to the primary (IgM) immune response which does not include T Cells. T cell dependent antigen responses are secondary responses. B cells possess surface immunoglobulin by which they are able to bind immunogens, the first step in their activation and clonal expansion. A single B cell expresses only one type of antigen-specific immunoglobulin. The site(s), region(s) or domain(s) of the immunogen to which the immunoglobulin binds is called a "B cell epitope." In the second step of B cell activation and expansion, T cells are activated through interaction with a site, region or domain of the immunogen called a "T cell epitope" which is presented by B cells or other antigen-presenting cells. Once activated, the T cells provide positive signal(s) to the B cells to which the immunogen is bound and they proceed to differentiate and to produce and secrete antibody. Positive signals from the T cell include the secretion of lymphokines, and/or direct contact between the B cells and T cells. T cell epitopes may be different or more restricted in scope than B cell epitopes. As discussed above, in order for an immunogen to elicit T dependent antibodies, it must have epitopes recognized by both B and T cells.

Past attempts to treat antibody-mediated pathologies have involved both general and specific suppression of the immune response. General suppression has typically employed broad spectrum, nonspecific immunosuppressants such as cyclophosphamide or steroids. Because these nonspecific drugs suppress many aspects of the immune system, they limit its required and beneficial functions as well as the malfunction causing the condition being treated. They are thus used only with extreme caution and subject the patient to risk from secondary infections or other undesirable side effects.

Because of the disadvantages of general immunosuppression, methods for specifically suppressing an immune response to an immunogen without affecting the normal functions of the immune system are highly preferred for treating antibody-mediated pathologies. The present invention concerns compositions and methods for specifically suppressing the humoral response to immunogens.

Prior attempts to induce specific immunosuppression have focused on conjugating haptens and immunogens to nonimmunogenic polymeric carriers. Benacerraf, Katz and their colleagues used conjugates of haptens and antigens and copolymers of D-lysine and D-glutamic acid (formerly D-GL, hereinafter D-EK). Their initial studies involved conjugates of the synthetic hapten 2,4-dinitrophenyl (DNP) in guinea pigs and mice and showed the conjugates were capable of inducing humoral unresponsiveness. These initial studies were then extended to conjugates of other haptens and conjugates of immunogens. While the results with haptens were repeatable, and although their patents (U.S. Pat. Nos. 4,191,668 and 4,220,565) allege the approach is effective in inducing tolerance to immunogens, subsequent work has shown that conjugates of D-EK and immunogens do not provide a means for inducing humoral unresponsiveness to the immunogen. For instance, Liu et al., *J. Immun.* (1979) 123:2456–2464, report that subsequent studies of those conjugates demonstrate that the conjugates "do not induce unresponsiveness at the level of protein specific B cells." Similarly, Butterfield et al., *J. Allergy Clin. Immun.* (1981) 67:272–278, reported that conjugates of ragweed immunogen and D-EK actually stimulated both IgE and IgG responses to the immunogen.

This subsequent work and other data dealing with conjugates of nonimmunogenic polymers and immunogens (Saski et al., *Scand. J. Immun.* (1982) 16:191–200; Sehon, *Prog. Allergy* (1982) 32:161–202; Wilkinson et al., *J. Immunol.* (987) 139:326–331, and Borel et al., *J. Immunol. Methods* (1990) 126:159–168) appear to indicate that the anergy, if any, obtained with such conjugates is due to suppression by T cells to directly suppress the immune response.

Several other references deal with conjugates of nonimmunogenic polymers and DNA. See U.S. Pat. Nos. 4,191,668; 4,650,625; *J. Clin. Invest.* (1988) 82:1901–1907; and commonly owned U.S. patent application Ser. No. 07/494,118. As a whole, these references indicate that these DNA conjugates may suppress the production of antibodies to this lupus autoimmunogen. It should be noted in this regard that DNA is not immunogenic and does not possess T cell epitopes.

In sum, applicants believe the prior art shows that antibody production to conjugates of nonimmunogenic stable polymers and haptens or DNA, neither of which have T cell epitopes, may provide B cell unresponsiveness. Applicants also believe that conjugates of immunogens do not provide B cell unresponsiveness but may activate T cells to directly suppress the immune response.

DISCLOSURE OF THE INVENTION

The present invention resides in the discovery that the failure of the prior conjugates of nonimmunogenic polymers and immunogens to induce B cell anergy (unresponsiveness) was due to the fact that the immunogens contained both B and T cell epitopes and that if the latter were eliminated, the conjugate would be effective for inducing B cell anergy.

Accordingly, one aspect of the invention is a composition for inducing specific B cell anergy to an immunogen comprising a conjugate of a nonimmunogenic valency platform molecule and an analog of the immunogen that (a) binds specifically to B cells to which the immunogen binds and (b) lacks the T cell epitope(s) of the immunogen.

Pharmaceutical compositions of the above-described conjugates and pharmaceutically acceptable carriers or vehicles are another aspect of the invention.

A further aspect of the invention is a method of inducing specific B cell anergy to an immunogen in an individual comprising administering to the individual an effective amount of the above-described conjugate.

Yet another aspect of the invention is a method of treating an individual for an antibody-mediated pathology in which undesired antibodies are produced in response to an immunogen comprising administering to the individual a therapeutically effective amount of the above-described conjugate.

BRIEF DESCRIPTION OF THE DRAWINGS

FIG. 1 graphically illustrates the detection of B cell epitopes in immunized CAF1 mice as described in Example 1. The unconjugated 17 mer peptide (L-42) and L-42 and L-53 D-EK conjugates were tested for B cell epitopes with anti-MIR sera. Unconjugated L-42 and L-53 were tested with normal mouse serum (NMS) as a control.

FIG. 2, similarly, illustrates the detection of T cell epitopes as described in Example 1.

FIG. 3 illustrates the suppression of antibodies to peptide "L-53" as described in Example 1.

FIGS. 4 and 5 are graphs of the results described in Example 4.

FIG. 6 compares the level of T cell proliferation induced by melittin peptides.

FIG. 7 compares the levels of anti-melittin peptide 2 antibodies produced in mice treated with Conjugate 2 versus the control mice treated with formulation buffer.

FIG. 8 compares the levels of anti-melittin antibodies produced in mice treated with Conjugate 2 versus the control mice treated with formulation buffer.

FIG. 9 compares the levels of anti-melittin peptide 2 antibody-forming cells in mice treated with Conjugate 2 versus the control mice treated with formulation buffer.

FIG. 10 illustrates that Conjugate 4, a conjugate of peptide #5 which contains a T cell epitope, was not a tolerogen.

FIG. 11 illustrates melittin conjugates within the present invention.

MODES FOR CARRYING OUT THE INVENTION

As used herein the term "B cell anergy" intends unresponsiveness of those B cells requiring T cell help to produce and secrete antibody and includes, without limitation, clonal deletion of immature and/or mature B cells and/or the inability of B cells to produce antibody. "Unresponsiveness" means a therapeutically effective reduction in the humoral response to an immunogen. Quantitatively the reduction (as measured by reduction in antibody production) is at least 50%, preferably at least 75%, and most preferably 100%.

"Antibody" means those antibodies which are T cell dependent.

As used herein the term "immunogen" means a chemical entity that elicits a humoral immune response when injected into an animal. Immunogens have both B cell epitopes and T cell epitopes.

The term "analog" of an immunogen intends a molecule that (a) binds specifically to an antibody to which the immunogen binds specifically and (b) lacks T cell epitopes. Although the analog will normally be a fragment or derivative of the immunogen and thus be of the same chemical class as the immunogen (e.g., the immunogen is a polypeptide and the analog is a polypeptide), chemical similarity is not essential. Accordingly, the analog may be of a different chemical class than the immunogen (e.g., the immunogen is a carbohydrate and the analog is a polypeptide) as long as it has the functional characteristics (a) and (b) above. The analog may be a peptide, carbohydrate, lipid, lipopolysaccharide, nucleic acid or other biochemical entity. Further, the chemical structure of neither the immunogen nor the analog need be defined for the purposes of this invention.

An analog of an immunogen may also comprise a "mimotope." The term "mimotope" intends a synthetic molecule which competitively inhibits the antibody from binding the immunogen. Because it specifically binds the antibody, the mimotope is considered to mimic the antigenic determinants of the immunogen. Like an analog of an immunogen, a mimotope (a) binds specifically to an antibody to which the immunogen binds specifically and (b) lacks T cell epitopes.

An analog of an immunogen may also comprise an "aptamer." The term "aptamer" intends a synthetic oligonucleotide which competitively inhibits the antibody from binding the immunogen. Like an analog of an immunogen, an aptamer (a) binds specifically to an antibody to which the immunogen binds specifically and (b) lacks T cell epitopes.

As used herein "valency platform molecule" means a nonimmunogenic molecule containing sites which facilitate the attachment of a discreet number of analogs of immunogens.

"Nonimmunogenic" is used to describe the valency platform molecule and means that the valency platform molecule elicits substantially no immune response when it is administered by itself to an individual.

As used herein "individual" denotes a member of the mammalian species and includes humans, primates, mice and domestic animals such as cattle and sheep, sports animals such as horses, and pets such as dogs and cats.

Immunogens that are involved in antibody-mediated pathologies may be external (foreign to the individual) immunogens such as allergens, Rh hemolytic disease (D immunogen), biological drugs, including native biological substances foreign to the individual such as therapeutic proteins, peptides and antibodies, and the like or self-immunogens (autoimmunogens) such as those associated with thyroiditis (thyroglobulin), stroke (cardiolipin), male infertility (α-sperm), myasthenia gravis (acetylcholine receptor) and rheumatic-fever (carbohydrate complex).

Analogs to such immunogens may be identified by screening candidate molecules to determine whether they (a) bind specifically to serum antibodies to the immunogen and (b) lack T cell epitopes. Specific binding to serum antibodies may be determined using conventional immunoassays and the presence or absence of T cell epitopes may be determined by conventional T cell activation assays. In this regard an analog which "binds specifically" to serum antibodies to the immunogen exhibits a reasonable affinity thereto. The presence or absence of T cell epitopes may be determined using the tritiated thymidine incorporation assay described in the examples. The presence of T cell eptiopes can also be determined by measuring secretion of T cell-derived lymphokines by methods well known in the art. Analogs that fail to induce statistically significant incorporation of thymidine above background are deemed to lack T cell epitopes. It will be appreciated that the quantitative amount of thymidine incorporation may vary with the immunogen. Typically a stimulation index below about 2–3, more usually about 1–2, is indicative of a lack of T cell epitopes.

A normal first step in identifying useful analogs is to prepare a panel or library of candidates to screen. For instance, in the case of protein or peptide analogs, libraries may be made by synthetic or recombinant techniques such as those described by Geysen et al. in *Synthetic Peptides as Antigens;* Ciba Symposium (1986) 119:131–149; Devlin et al., *Science* (1990) 249:404–406; Scott et al., *Science* (1990) 249:386–390; and Cwirla et al., *PNAS USA* (1990) 87:6378–6382. In one synthetic technique, peptides of about 5 to 30 amino acids are synthesized in such a manner that each peptide overlaps the next and all linear epitopes are represented. This is accomplished by overlapping both the carboxyl and amino termini by one less residue than that expected for a B cell epitope. For example, if the assumed minimum requirement for a B cell epitope is six amino acids, then each peptide must overlap the neighboring peptides by five amino acids. In this embodiment, each peptide is then screened against antisera produced against the native immunogen, either by immunization of animals or from patients, to identify the presence of B cell epitopes. Those molecules with antibody binding activity are then screened for the presence of T cell epitopes as described in the examples. The molecules lacking T cell epitopes are useful as analogs in the invention.

If the T cell epitope(s) of an immunogen are known or can be identified, random T cell screening of candidate analogs is not necessary. In such instances, the T cell epitope(s) may be altered (e.g., by chemical derivatization, or elimination of one or more components of the epitope) to render them inoperative or be eliminated completely, such as, for instance, in the case of peptides, by synthetic or recombinant procedures.

Mimotopes and aptamers are synthesized by conventional methods and are screened in the same manner as other analogs of immunogens.

The analogs are coupled to a nonimmunogenic valency platform molecule to prepare the conjugates of the invention. Preferred valency platform molecules are biologically stabilized, i.e., they exhibit an in vivo excretion half-life often of hours to days to months to confer therapeutic efficacy, and are preferably composed of a synthetic single chain of defined composition. They will normally have a molecular weight in the range of about 200 to about 200,000, usually about 200 to about 20,000. Examples of valency platform molecules within the present invention are polymers such as PEG, poly-D-lysine, polyvinyl alcohol, polyvinylpyrrollidone, immunoglobulins, and D-EK. Preferred polymers are based on polyethylene glycols (PEGs) having a molecular weight of about 200 to about 8,000. Other preferred polymers are D-EKs having a molecular weight of about 5,000 to about 30,000, and an E:K (D-glutamic acid:D-lysine) mole ratio of approximately 60:40, as described in U.S. patent application Ser. No. 07/494,118; referenced above.

Conjugation of the analog to the valency platform molecule may be effected in any number of ways, typically involving one or more crosslinking agents and functional groups on the analog and valency platform molecule.

Polypeptide analogs will contain amino acid sidechain groups such as amino, carbonyl, or sulfhydryl groups that will serve as sites for coupling the analog to the carrier. Residues that have such functional groups may be added to the analog if the analog does not already contain same. Such residues may be incorporated by solid phase synthesis techniques or recombinant techniques, both of which are well known in the peptide synthesis arts. In the case of carbohydrate or lipid analogs, functional amino and sulfhydryl groups may be incorporated therein by conventional chemistry. For instance, primary amino groups may be incorporated by reaction with ethylenediamine in the presence of sodium cyanoborohydride and sulfhydryls may be introduced by reaction of cysteamine dihydrochloride followed by reduction with a standard disulfide reducing agent. In a similar fashion the valency platform molecule may also be derivatized to contain functional groups if it does not already possess appropriate functional groups. With specific reference to conjugating peptide analogs and D-EK or other proteinaceous valency platform molecules, coupling is preferably carried out using a heterobifunctional crosslinker, such as sulfosuccinimidyl (4-iodoacetyl) aminobenzoate, which links the $\epsilon$ amino group on the D-lysine residues of D-EK to a sulfhydryl side chain from an amino terminal cysteine residue on the peptide to be coupled. This method is usually carried out such that an average of 3 to 5 analog molecules are coupled to each D-EK molecule and the average molecular weight of the D-EK prior to coupling is 5,000 to 30,000 daltons.

The conjugates will normally be formulated for administration by injection (e.g., intraperitoneally, intramuscularly, etc.). Accordingly, they will typically be combined with pharmaceutically acceptable vehicles such as saline, Ringer's solution, dextrose solution, and the like. The conjugate will normally constitute about 0.01% to 10% by weight of the formulation. The conjugate is administered to an individual in a "therapeutically effective amount", i.e., an amount sufficient to produce B cell anergy to the involved immunogen and effect prophylaxis, improvement or elimination of the antibody-mediated condition being addressed. The particular dosage regimen, i.e., dose, timing and repetition, will depend on the particular individual and that individual's medical history. Normally, a dose of about 10 μg to 1 mg conjugate/kg body weight will be given, daily for three consecutive days. Other appropriate dosing schedules would be 3 doses per week, or one dose per week, or one dose every two to four weeks, or one dose on a monthly or less frequent schedule depending on the individual or the disease state. Repetitive administrations, normally timed according to B cell turnover rates may be required to achieve and/or maintain a state of humoral anergy. Such repetitive administrations will typically involve treatments of up to 1 mg/kg of body weight every 30 to 60 days, or sooner, if an increase in antibody titer is detected. Alternatively, sustained continuous release formulations of the conjugates may be indicated for some pathologies. Various formulations and devices for achieving sustained release are known in the art.

Anti-T helper cell treatments may be administered together with the conjugates. Such treatments usually employ agents that suppress T cells such as steroids or cyclosporin.

The following examples are intended to further illustrate the invention and its uniqueness. These examples are not intended to limit the scope of the invention in any manner.

EXAMPLE 1

B Cell Anergy to the Acetylcholine Receptor

Preparation of Peptides and D-EK/Peptide Conjugates:

The α-subunit of the acetylcholine receptor of *Torpedo californicus* is described by Stroud, R. M., and Finer-Moore, J., *Ann. Rev. Cell Biol.* (1985) 1:317:351, and Sumikawa, K., et al., *Nucl. Acids Res.* (1982) 10:5809–22. The peptide defined by residues 47–127 of that α-subunit is called the major immunogenic region (MIR).

Two peptides, L-42 and L-53, corresponding to residues 61–77 and 112–127 of that α-subunit, were synthesized using conventional solid-phase methods and purified to homogeneity by HPLC. An amino terminal cysteine was added to each sequence for the purpose of attachment of the peptide to D-EK via a thio ether linkage.

Each peptide (40 mg) was dissolved in 0.1 M sodium borate buffer, pH 9.0. The solution was reacted with citraconic anhydride (400 μL) at room temperature; the pH was maintained above 7.0 by addition of 1 M NaOH. The solution was then made 20 mM in dithiothreitol and was warmed at 37° C. for 20 minutes to reduce the peptide. The mixture was quickly desalted over G-10 Sephadex columns which were equilibrated with 0.1M sodium borate, pH 7.0.

D-EK (200 mg, weight average molecular weight ≈10,000–30,000) was dissolved in 2.0 mL of 0.1M sodium borate. Sulfosuccinimidyl (4-iodoacetyl) aminobenzoate (SSIAB, 10 mg, Pierce Chemical) was added to the mixture and the mixture was reacted for 90 minutes at room temperature in the dark. The mixture was then desalted over a 10 mL G-25 column, equilibrated with 0.1M sodium borate, pH 7.0.

The desalted SSIAB-D-EK was mixed with the reduced and desalted peptide and reacted overnight. The resulting conjugate was placed in dialysis tubing with a 14 Kd cutoff and was dialyzed against 5% acetic acid to remove citraconyl groups. The dialysis buffer was changed to phosphate-buffered saline and the dialysis continued.

Detection of B Cell Epitopes:

CAF1 mice were obtained and housed at the La Jolla Pharmaceutical animal facility according to National Institutes of Health guidelines. CAF1 mice were immunized (day 0) intraperitoneally (i.p.) with 50 μg of recombinant torpedo MIR absorbed onto alum plus *B. pertussis* vaccine (*B. pertussis* vaccine obtained from Michigan Department of Public Health, Lansing, Mich.) (Iverson, G. M., (1986) *Handbook of Experimental Immunology*, Vol.2, p. 67, D. M Weir ed., Blackwell Scientific Publications, Palo Alto, Calif.). The mice received a booster injection of the same protein in saline, i.p., on day 21 and were bled from the tail vein on day 28. Sera from these mice (anti-MIR sera) were used to screen peptides L-42 and L-53 for the presence of B cell epitopes, as follows. The sera were added to the wells of microtitration plates which were coated with 10 μg/mL of the indicated peptide conjugates. The plates were incubated at 37° C. for one hour, washed 3 times, 100 μl of alkaline phosphatase-conjugated goat anti-mouse antibody was added, incubated at 37° C. for one hour, washed 3 times, and 100 μl of developer (substrate) was added to each well. The plates were incubated at room temperature for 30 minutes and the amount of color in each well was determined in a Titertek® Multiskan microplate reader. Results are illustrated graphically in FIG. 1. The curve labelled "L42 or L53, NMS" contains the values obtained using normal mouse serum (NMS) instead of the anti-MIR sera on plates coated with either L42 or L53. As shown in FIG. 1, both peptides reacted specifically with antibodies from the immunized mice indicating the presence of B cell epitopes on both peptides.

Figure 2:
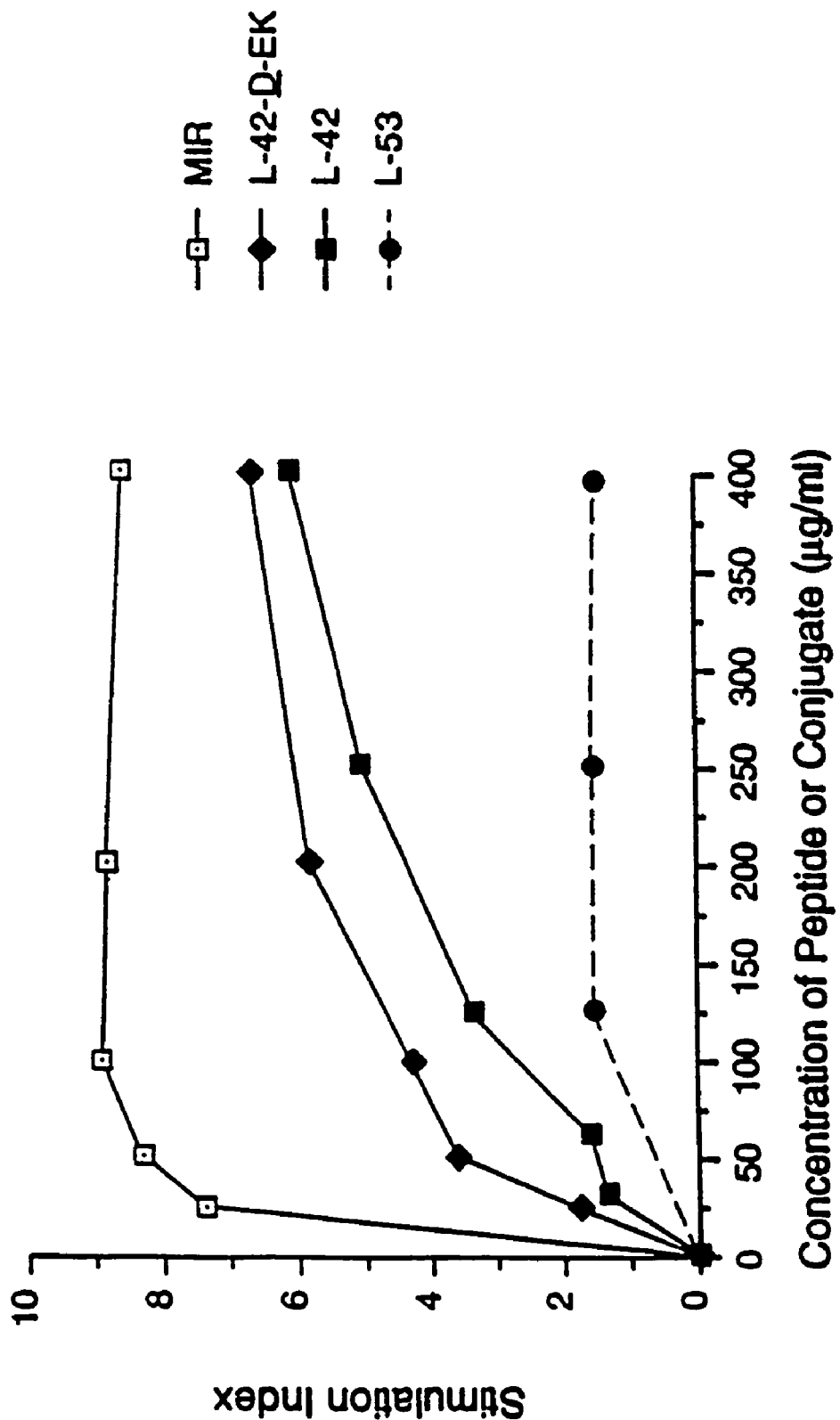

Detection of T Cell Epitopes:

T cell activation was assayed by the general procedure of Bradley, M. L., (1980) in Mishell and Shigii, eds., *Selected Methods in Cellular Immunology* (W.H. Freeman and Co., San Francisco, Calif.), p. 164. CAF1 mice were obtained and housed at the La Jolla Pharmaceutical animal facility according to National Institutes of Health guidelines. CAF1 mice were immunized in the footpad with 50 μg MIR in Complete Freund's Adjuvant (CFA) on day 0. On day 7 the popliteal lymph nodes were removed and placed in culture in microtiter plates using $5 \times 10^5$ cells per well. The peptides or peptide-DEK conjugate were added to the cultures, and on day 4, 1 μCi of tritiated thymidine was added to each well to measure proliferation of T cells. The cultures were harvested on day 5 with a Skatron® cell harvester. The amount of incorporated $^3$H-thymidine was determined in a Beckman L6800® liquid scintillation counter. The stimulation index was calculated by dividing the CPM incorporated with peptide by the CPM incorporated from cultures without any peptide. A stimulation index >2–3 was indicative of the presence of a T cell epitope on the peptide added to the well. As shown in FIG. 2, L-42 but not L-53 possessed T cell epitopes in this assay.

Figure 3A:
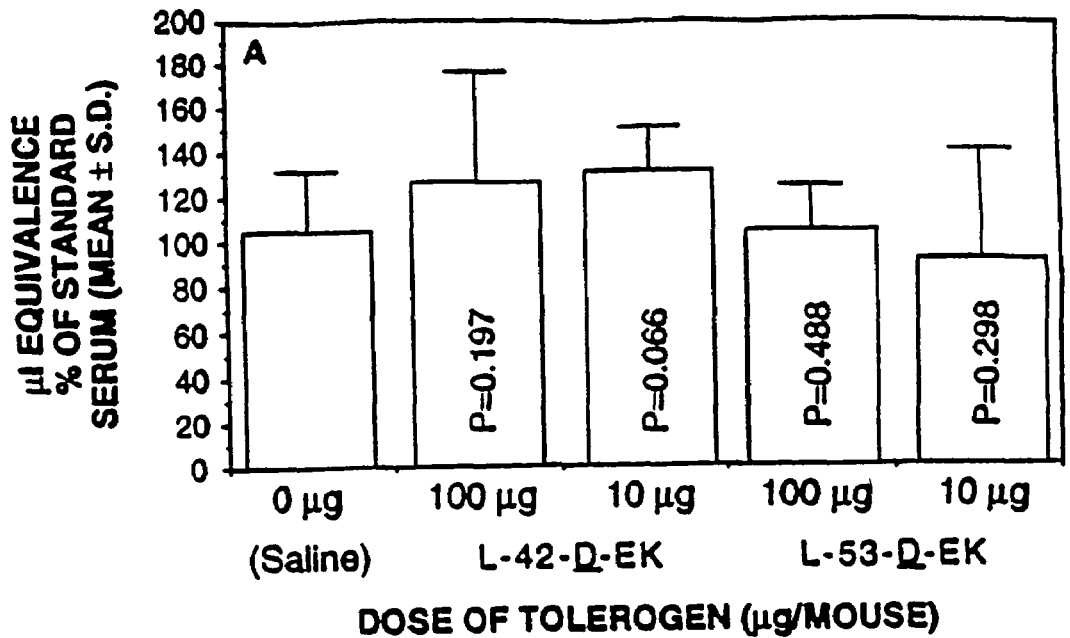
Figure 3B:
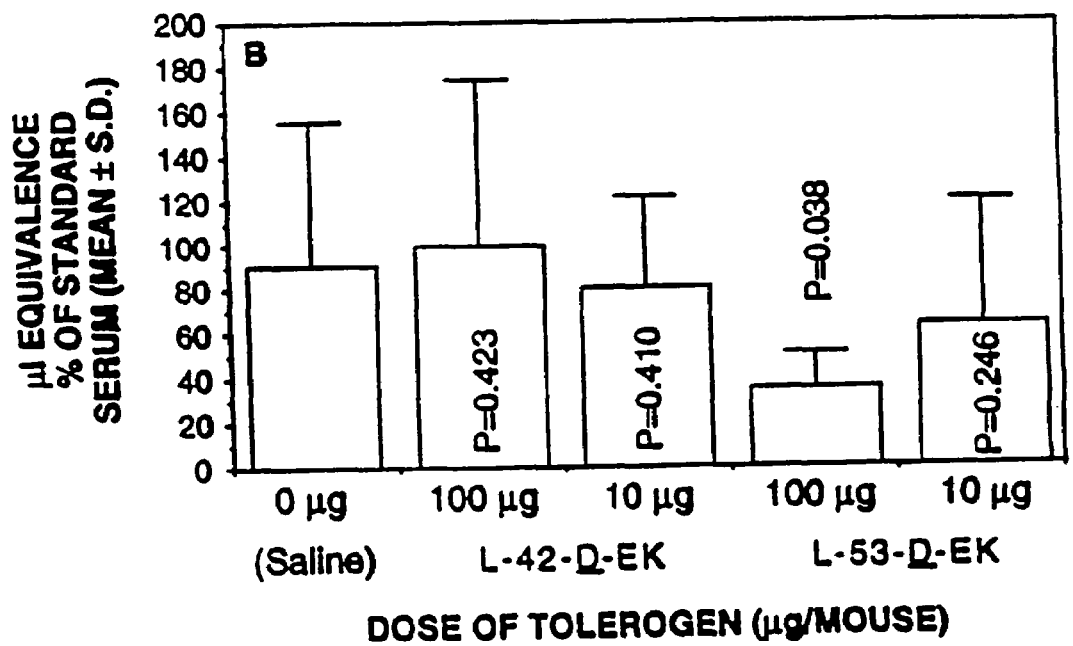

Induction of B Cell Anergy to L-53 by L-53-D-EK Conjugate:

CAF1 mice were obtained and housed at the La Jolla Pharmaceutical animal facility according to National Institutes of Health guidelines. CAF1 mice were immunized with 50 μg of MIR, i.p., absorbed onto alum plus *B. pertussis* vaccine on day 0. On days 21, 22 and 23 the mice (6 mice per group) received 10 or 100 μg of either L-42-D-EK conjugate or L-53-D-EK conjugate. One group received only saline. On day 28 all mice received a booster injection of MIR in saline and on day 35 all mice were bled and assayed for the presence of antibodies to L-42 and L-53 in their sera, using an ELISA assay as described above with respect to FIG. 1. The results for antibodies to L-42 are shown in FIG. 3A and for antibodies to L-53 are shown in FIG. 3B. The L-53 conjugate, which did not contain a T cell epitope, suppressed antibody formation to L-53 but not to L-42. The L-42 conjugate, which contained a T cell epitope, did not suppress the antibody response to either L-42 or L-53, but rather may have increased antibody production to L-42. The antibody titers are expressed as a percent of a standard sera. The P values were determined by a Student t test comparing each dose to the saline control.

EXAMPLE 2

Failure of Ovalbumin-D-EK Conjugate to Induce B Cell Anergy to Ovalbumin

This example is further evidence that conjugates of immunogens and D-EK do not induce B cell anergy.

Synthesis of Ovalbumin-D-EK Conjugate:

Chicken egg ovalbumin (ova; 50 mg) was dissolved in 5 mL of 0.1M sodium borate buffer, pH 9.0, containing 10 mM EDTA. After the addition of 3.0 mg of 2-iminothiolane (Traut's reagent), the mixture was reacted for 2.5 hours at room temperature. D-EK (54 mg), dissolved in 0.5 M sodium borate, pH 9.0, at a concentration of 100 mg/mL, was reacted with SSIAB (18 mg; Pierce Chemical) for 2.5 hours in the dark, at room temperature. The two reaction mixtures described above were desalted separately on G-25 columns (Pharmacia; 10 mL column volume, equilibrated with 0.1 M sodium borate, pH 9.0) and the excluded fractions were combined and reacted for 16 hours at 4° C., in the dark. The reaction product was fractionated by gel filtration over Sephacryl S-200 (490 mL, Pharmacia) columns, equilibrated with 0.2 M ammonium bicarbonate. Fractions containing conjugate, as assessed by polyacrylamide gel electrophoresis, in the presence of sodium dodecyl sulfate (SDS-PAGE), were pooled and dried under vacuum. The dried material was reacted with 0.8 mL of citraconic anhydride, maintaining the pH between 7 and 9 by the addition of 1M NaOH, in order to efficiently separate conjugated ovalbumin from unreacted protein. The citraconylated conjugate was rechromatographed over S-200, and fractions containing high molecular, weight material (>80,000 daltons), as assessed SDS-PAGE; were used for biological studies.

Chicken Ovalbumin, when Conjugated to D-EK, does not include B Cell Anergy in Mice Immunized to Chicken Ovalbumin:

CAF1 mice were obtained and housed at the La Jolla Pharmaceutical animal facility according to National Institutes of Health guidelines. Female $CAF_1$ mice were primed with ova (100 μg/mouse, i.p.) precipitated on alum, with *B. pertussis* vaccine added as an adjuvant. Sixteen weeks later, the mice were divided into two groups of six mice each. One group (control) was treated with saline, and the second group was injected with a conjugate of ova and D-EK (ova-D-EK; 200 μg/mouse/day, i.p.). The mice were dosed on three successive days. One week after the first dose, the mice in both groups were boosted, i.p., with ova in saline (100 μg/mouse). One week later, the mice were bled from a tail vein. The plasma was harvested and assayed for the amount of anti-ova antibodies by an ELISA assay. As shown in Table 1, the ova-D-EK conjugate did not suppress the anti-ova response.

TABLE 1

| Group | Treatment | Percent of Anti-Ova Standard[1] Serum ± S.D. |
|---|---|---|
| 1 | saline | 70.7 ± 36 |
| 2 | ova-D-EK | 160.2 ± 167 |

[1]The amount of anti-ova antibody was determined in an ELISA, measured against a standard pool of sera obtained from CAP, mice immunized and boosted with ova. The values shown are the mean and standard deviation for the six mice in each group.

EXAMPLE 3

Failure of MIR-D-EK Conjugate to Induce B Cell Anergy to MIR

This example is still further evidence that conjugates of immunogens and D-EK do not induce B cell anergy.

Synthesis of MIR-D-EK Conjugate:

MIR was modified on its carboxyl-terminus to include a sequence of 8-amino acids (Arg-Ser-Lys-Ser-Lys-Ser-Lys-Cys (SEQ. ID NO.: 1)). The amino-terminus was extended by one amino acid, proline. Purified modified MIR (250 mg) was reduced with 100 mM dithiothreitol and was desalted over Sephadex G-25 (Pharmacia), equilibrated with 0.1 M sodium borate buffer, pH 9.0, containing 10 mM EDTA. D-EK (400 mg) was reacted with SSIAB (29 mg) as in the previous examples. The product was desalted over G-25. The excluded volumes from the modified MIR and D-EK G-25 column runs were combined and reacted at 4° C. for 16 hours, in the dark. Excess SSIAB groups were quenched with 2-mercaptoethanol, and the reaction mixture was concentrated to 20 mL over a PM-10 membrane (Amicon Corporation). The mixture was treated with 1.0 mL of citraconic anhydride and chromatographed over S-300 (Pharmacia; 1.8 L), equilibrated with 5% ammonium hydroxide. Fractions containing two or more modified MIR groups per D-EK; as assessed by SDS-PAGE, were pooled and used for biological studies.

MIR-D-ER Conjugate Contains T Cell Epitopes Recognized by Rats Immunized with MIR from the Same Species:

T cell activation was assayed by the general procedure of Bradley, supra. Female Lewis rats were immunized in the footpad with MIR (50 μg) in complete Freund's adjuvant (CFA) on day 0. On day 7, the popliteal lymph nodes were removed and placed in culture in microtiter plates using 5–$10^5$ cells per well. MIR-D-EK was added, and, after, four days of culture, the wells were pulsed with tritiated thymidine (1-μCi) to measure proliferation of T cells. The cultures were collected after 5 days of culture with a Skatron™ cell harvester. The amount of incorporated $^3$H-thymidine was determined by scintillation spectrometry. The stimulation index was calculated by dividing the counts incorporated in the absence of the conjugate. A stimulation index of greater than 2–3 was considered indicative of the presence of a T cell epitope on the added conjugate. The stimulation index was 4 or greater at all concentrations of MIR-D-EK tested (10 μg/mL to 400 mg/mL), proving that T cells from MIR-immunized rats recognize T cell epitopes on the MIR-D-EK conjugate in this assay.

MIR-D-EK does not Induce B Cell Anergy in Rats Immunized with MIR:

Female Lewis rats were primed with MIR (100 μg/rat) in CFA. Six months later, the rats were divided into three groups of three rats each. One group was treated with saline (control) and the other two groups were treated with MIR-D-EK (100 μg/rat, i.p.) on three successive days. After one week, the rats in the control group and one group that had been treated with MIR-D-EK were boosted with recombinant MIR (1000 μg/rat, i.p.) in saline. One week later, all three groups of rats were bled from the tail vein. The plasma was harvested and assayed for the amount of anti-MIR antibodies by an ELISA assay. Table 2 below reports the data from those assays.

TABLE 2

| Group | Treatment | MIR Boost | μLequivalence (% of standard anti-MIR[1]) (mean ± S.D.) | P. vs. Group 1 |
|---|---|---|---|---|
| 1 | Saline | Yes | 130.5 ± 74.7 | |
| 2 | MIR-D-EK | Yes | 85.5 ± 31.1 | 0.195 |
| 3 | MIR-D-EK | No | 230.6 ± 31 | 0.049 |

[1]The concentration of anti-MIR antibodies was determined in an ELISA measured against a standard pool of rat anti-MIR sera. The values shown are the mean and standard deviation of the three rats in each group. P values were determined by a Student t test. Group 2 is not significantly different from Group 1. Group 3 (the non-boosted group) is significantly higher than Group 1.

As shown in Table 2, the data on Group 1 animals (saline control) indicate that MIR itself is an immunogen. The data for the Group 2 and 3 animals indicate that the MIR-D-EK conjugate did not suppress the anti-MIR response. In fact, MIR-D-EK boosted the anti-MIR response in Group 3.

These tests, taken together with the results of Example 1 show that the moiety conjugated to D-EK will cause anergy in B cells recognizing that moiety if the moiety either does not contain a T cell epitope or is not recognized by T cells.

EXAMINE 4

Tests with Conjugate of L-42 and KLH

Synthesis of L-42 Peptide-KLH Conjugate:
Reduced L-42 (see Example 1) was conjugated to keyhole limpet hemocyanin (KLH) using thioether chemistry similar to that described above with respect to D-EK.

L-42 does not Activate T Cells in Mice Immunized with L-42-KLH:
Activation of T cells by peptides was measured by the general procedure of Bradley, supra. Female $CAF_1$ mice were immunized in the footpad with L-42 peptide conjugated KLH (L-42-KLH; 50 μg) in CFA on day 0. On day 7, the popliteal lymph nodes were removed and placed in culture in microtiter plates, at a cell density of $5 \cdot 10^5$ cells/well. Peptides were added, and, after four days of culture, the wells were pulsed with 1 μCi of tritiated thymidine to measure proliferation of T cells. The cultures were collected after 5 days of culture with a Skatron™ cell harvester. The amount of incorporated $^3$H-thymidine was determined by scintillation spectrometry. The stimulation index was calculated by dividing the counts incorporated in the absence of peptide. An index of greater than 2–3 is indicative of the presence of a T cell epitope on the added peptide.

Figure 4:
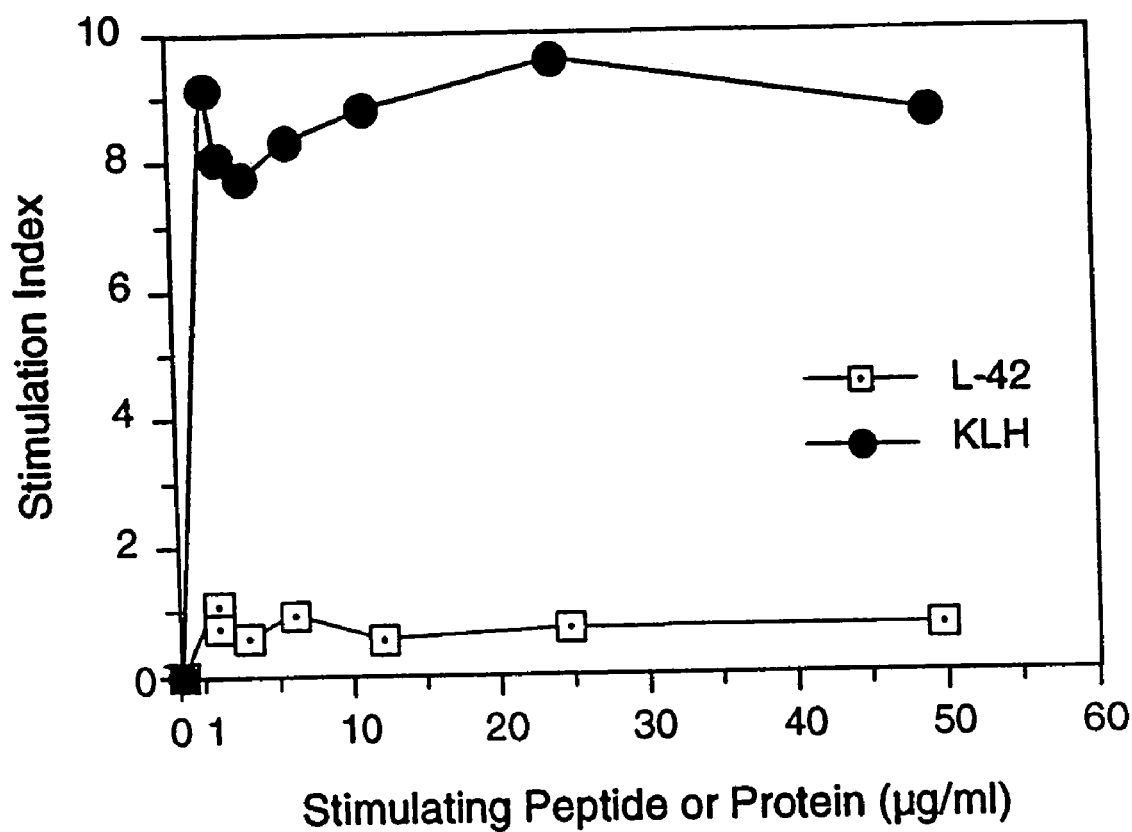

The data in FIG. 4 demonstrate that the L-42 did not stimulate the growth of T cells taken from L-42-KLH-immunized mice, and therefore did not contain an epitope(s) recognized by T cells induced by immunization with L-42-KLH.

L-42-D-EK Conjugate Induces a B Cell Anergy in Mice Immunized to L-42-KLH:
$CAF_1$ mice were primed with 100 μg/mouse of L-42-KLH on alum plus *B. pertussis* vaccine as an adjuvant. Three weeks later, the mice were divided into groups of six mice each. One group was treated by i.p. injections on three successive days with saline (control); the other groups were similarly treated with various doses of L-42-D-EK (i.p.). Five days later, all mice were boosted with L-42-KLH (50 μg/mouse), and, after a wait of one week, they were bled from the tail vein. The plasma was harvested and assayed for the amount of anti-L-42 and anti-KLH antibodies by ELISA assays. Data are expressed as a percent of a standard serum. An asterisk indicates that a data point was significantly different from the control as determined by a Student t test.

Figure 5:
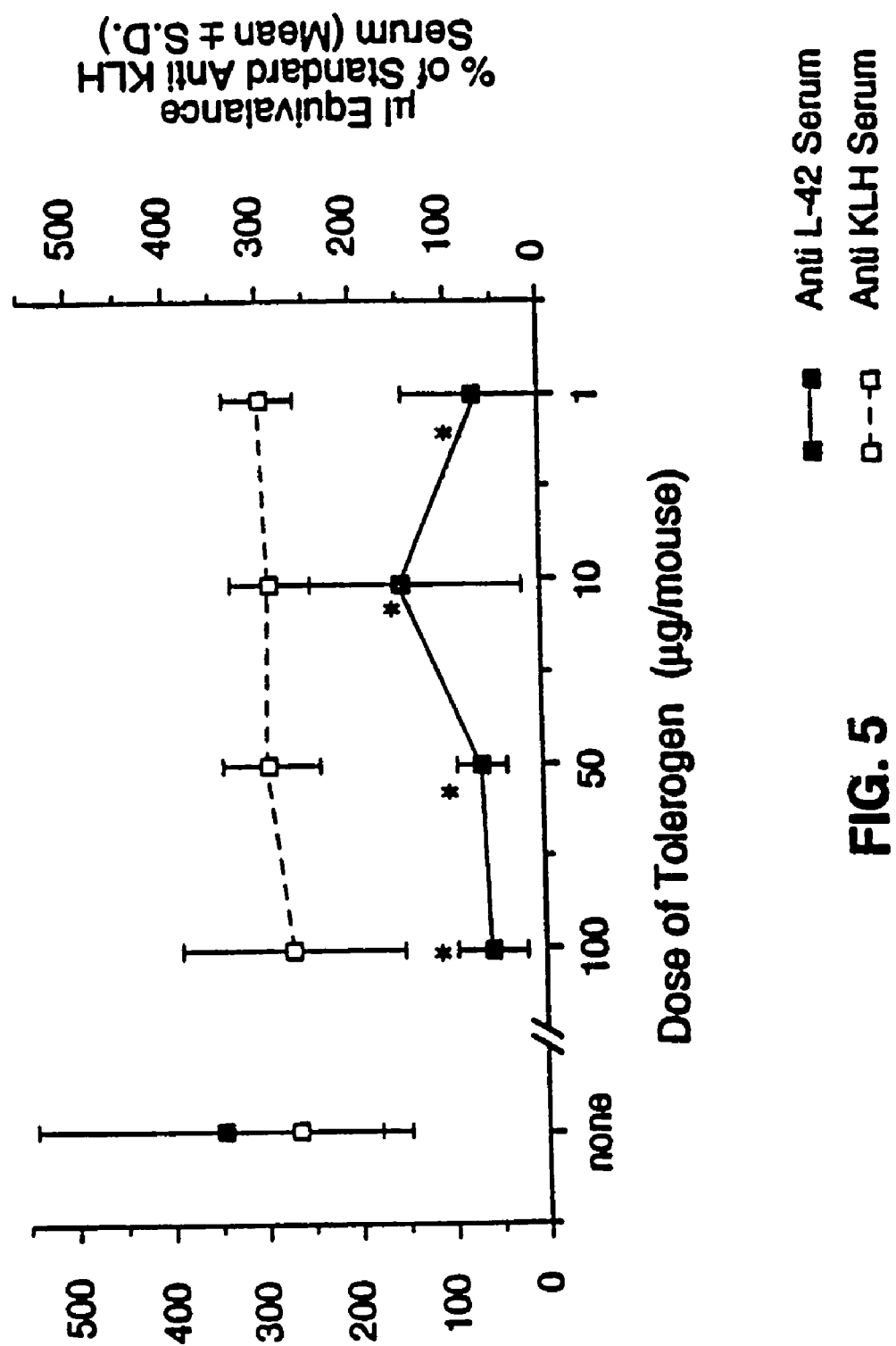

The data in FIG. 5 demonstrate that the anti-L-42 response, but not the anti-KLH response, was suppressed in this assay by the L-42-D-EK conjugate. Thus, the studies summarized in Example 1 and these data demonstrate the L-42-D-EK induces B cell anergy when the mice are immunized in a manner that does not induce the proliferation of T cell clones that recognize the L-42 peptide. This is in contrast to Example 1 where L-42-D-EK did not induce B cell anergy in animals that were immunized with an immunogen (MIR) which induced T cells that recognized the L-42 peptide.

EXAMPLE 5

Preparation of Melittin Peptides and Conjugates

The melittin molecule, composed of 26 amino acids, is one of the major components of bee venom. One third of the bee venom sensitive individuals have melittin specific antibodies. Melittin is highly immunogenic in some mouse strains (Balb/c, CAF1). The majority (>80%) of melittin-specific antibodies in the responder mouse strains bind a B cell epitope which is the C-terminal heptapeptide of melittin.

Melittin (SEQ. ID NO: 11)
H₂N-Gly-Ile-Gly-Ala-Val-Leu-Lys-Val-Leu-Thr-Thr-
Gly-Leu-Pro-Ala-Leu-Ile-Ser-Trp-Ile-Lys-Arg-Lys-
Arg-Gln-Gln-CONH₂.

Melittin Peptides for T Cell Stimulation

Melittin Peptide #1.
(SEQ. ID NO.: 2)
Ile-Lys-Arg-Lys-Arg-Gln-Gln-Gly
("7 mer").

Melittin Peptide #2.
(SEQ. ID NO.: 3)
Trp-Ile-Lys-Arg-Lys-Arg-Gln-Gln-Gly
("8 mer").

Melittin Peptide #3.
(SEQ. ID NO.: 4)
Ser-Trp-Ile-Lys-Arg-Lys-Arg-Gln-Gln-Gly
("9 mer").

Melittin Peptide #4.
(SEQ. ID NO.: 5)
Ile-Ser-Trp-Ile-Lys-Arg-Lys-Arg-Gln-Gln-Gly
("10 mer").

Melittin Peptide #5.
(SEQ. ID NO.: 6)
Cys-Ile-Ser-Trp-Ile-Lys-Arg-Lys-Arg-Gln-Gln-Gly
("10 mer + C").

Peptide Synthesis.
Melittin peptides were synthesized using standard Fmoc chemistry techniques on a glycine resin (Advanced ChemTech #SG5130 or equivalent (Advanced ChemTech, 2500 Seventh Street Road, Louisville, Ky.) using 2.3 M excess amino acid derivatives for each coupling step.

Completion of the coupling was monitored with bromphenol blue and confirmed with ninhydrin.

Melittin Peptides Used in Conjugations

```
Melittin Peptide #5.
                                    (SEQ. ID NO.: 7)
H2N-Cys-Ile-Ser-Trp-Ile-Lys-Arg-Lys-Arg-Gln- Gln-Gly-CO2H.

Melittin Peptide #6 - (Peptide #2 + C).
                                    (SEQ. ID NO.: 8)
H2N-Cys-Trp-Ile-Lys-Arg-Lys-Arg-Gln-Gln- Gly-CO2H.

Melittin Peptide #7.
                                    (SEQ. ID NO.: 9)
H2N-Trp-Ile-Lys-Arg-Lys-Arg-Gln-Gln-Lys-Cys- Gly-CO2H.

Melittin Peptide #8.
                                    (SEQ. ID NO.: 10)
(H2N-Trp-Ile-Lys-Arg-Lys-Arg-Gln-Gln)2-Lys-Cys- Gly-CO2H.
```

A cysteine was added as required for coupling certain peptides via a thioether bond to the valency platform molecule. Peptides were purified by reversed phase HPLC following synthesis and lyophilized to dryness. The appropriate amount of peptide was then weighed out for each conjugation.

Reduction of Preformed Disulfide Bonds:

(Tributylphosphine Method)

All buffers were sparged with helium. The peptide was dissolved in a minimal volume (approximately 10 to 20 mg/mL) of 0.05 M $NaHCO_3$ (pH 8.25). A 1 mL solution of 0.7 M tributylphosphine (TBP; MW=202.32 g/mole; d-0.812 g/mL was prepared by adding 174 μL of TBP to 826 μL of isopropanol (iPrOH). Then, 1:1 equivalents of TBP were added to the peptide solution prepared as described above, mixed well, and allowed to react for 30 minutes to 1 hour with occasional mixing to keep TBP dissolved and/or dispersed in the solution. Complete reduction was confirmed by HPLC.

Preparation of Valency Platform Molecules #3 or #5

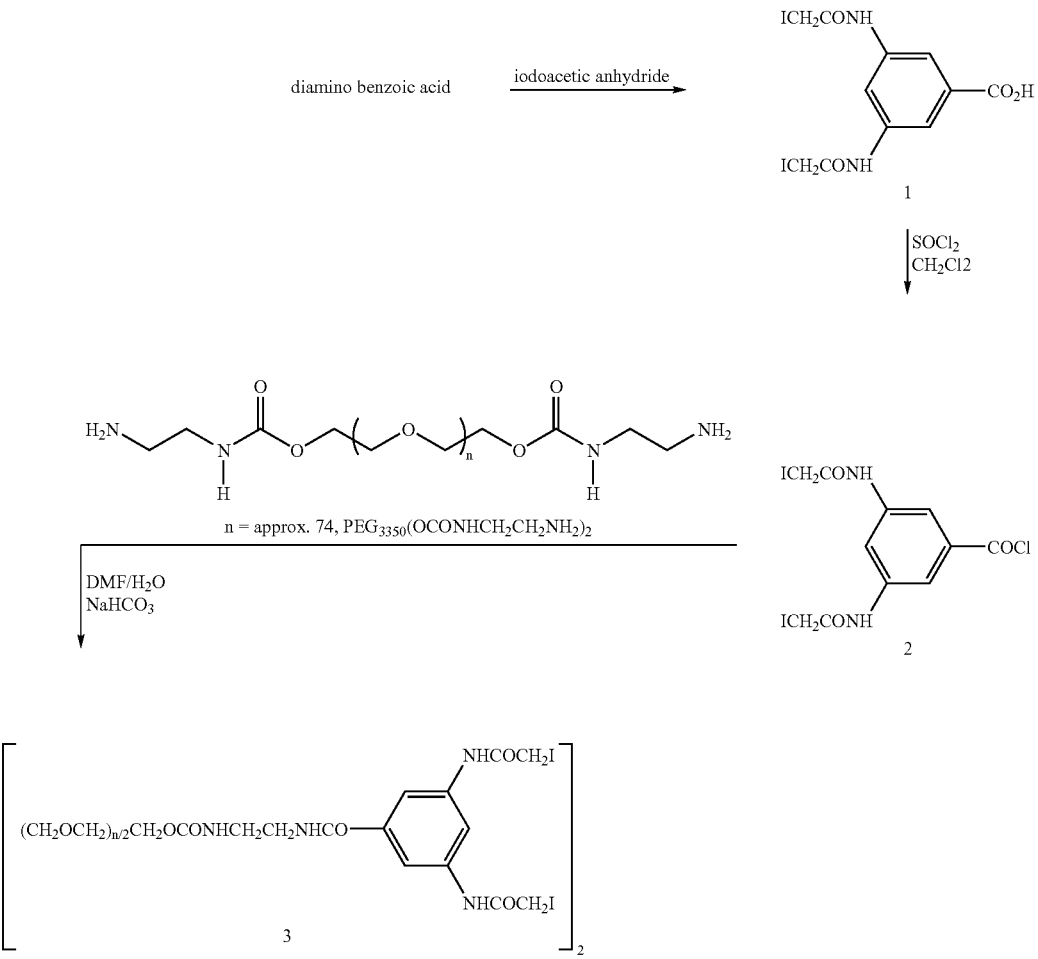

Reaction Scheme I

Compound 1—[3,5-Bis-(iodoacetamido)benzoic acid]

2.93 g (8.28 mmol, 2.2 eq) of iodoacetic anhydride was added to a stirred suspension of 572 mg (3.76 mmol) of 3,5-diaminobenzoic acid in 19 mL of dioxane at room temperature under $N_2$ atmosphere. The mixture was stirred, covered with foil for 20 hours and partitioned between 50 mL of EtOAc and 50 mL of 1 N HCl solution. The EtOAc layer was washed with brine, dried over $MgSO_4$, filtered, and concentrated on a rotary evaporator to give 3.3 g of tan solid. The material was purified by silica gel chromatography (94/5/1 $CH_2Cl_2$/MeOH/HOAc) to yield 992 mg (54%) of compound 1 as a white solid: NMR (DMSO) 3.84 (s, 4H), 7.91 (s, 2H), 8.14 (s, 1H), 10.56 (s, 2H).

Compound 2—[3.5-Bis-(iodoacetamido)benzoyl chloride]

117 µL (1.6 mmol, 190 mg) of $SOCl_2$ was added to a solution of 390 mg (0.8 mmol) of 1 in 34 mL of THF. The mixture was refluxed under $N_2$ atmosphere until all solids had dissolved (approximately 30 minutes) to give a clear red-brown solution. The mixture was concentrated on the rotary evaporator and placed under vacuum to provide crude compound 2 as a foamy solid which was used directly in the next step.

Compound 3—[N,N'-Bis-(3,5-bis-(iodoacetamido) benzoyl) derivative of α, w-bis-(N-2-aminoethyl-carbamoyl)polyethyleneglycol]

570 mg of α, w-bis-(N-2-aminoethylcarbamoyl)polyethyleneglycol (0.16 mmol, 3350 g/mol, Sigma) was placed in a tared flask. Toluene (20 mL) was added and water was removed by, azeotropic distillation. The residue was dried under vacuum to give 549 mg of solid and dissolved in 4 mL THF with 89 µL (0.64 mmol) of diisopropylethylamine. The crude acid chloride was dissolved in 4 mL anhydrous THF and added to the mixture over 30 seconds under $N_2$. The mixture was stirred for 16 hours at room temperature and partitioned between 25 mL of 0.1 N HCl and 25 mL of $CH_2Cl_2$. The aqueous layer was again extracted with $CH_2Cl_2$ and the organic layers were combined, washed with 25 mL of $H_2O$, followed by 50 mL of at $NaHCO_3$ solution. The organic layers were dried with $Na_2SO_4$, filtered, and concentrated to give 784 mg of orange oil. Silica gel chromatography (9/1 $CH_2Cl_2$/MeOH) yielded 190 mg of colorless oil which was crystallized from hot $EtOH/Et_2O$, collected on sintered glass filter under $N_2$ pressure, and dried under vacuum to provide 177 mg of compound 3 as a white solid: NMR ($CDCl_3$ 3.40 (bd m, 8H), 3.59 (bd s, $(CH_2CH_2O)_n$, integral too large to integrate in relation to other integrals), 3.80 (bd m, 4H), 3.91 (s, 8H), 7.49 (brd m, 2H), 7.77 (bd m, 2H), 7.82 (bd s, 4H), 8.27 (bd s, 2H), 8.90 (bd m, 4H): iodoacetyl determination (*European Journal of Biochemistry* (1984) 140:63–71): Calculated, 0.92 mmol/g; Found, 0.96 mmol/g.

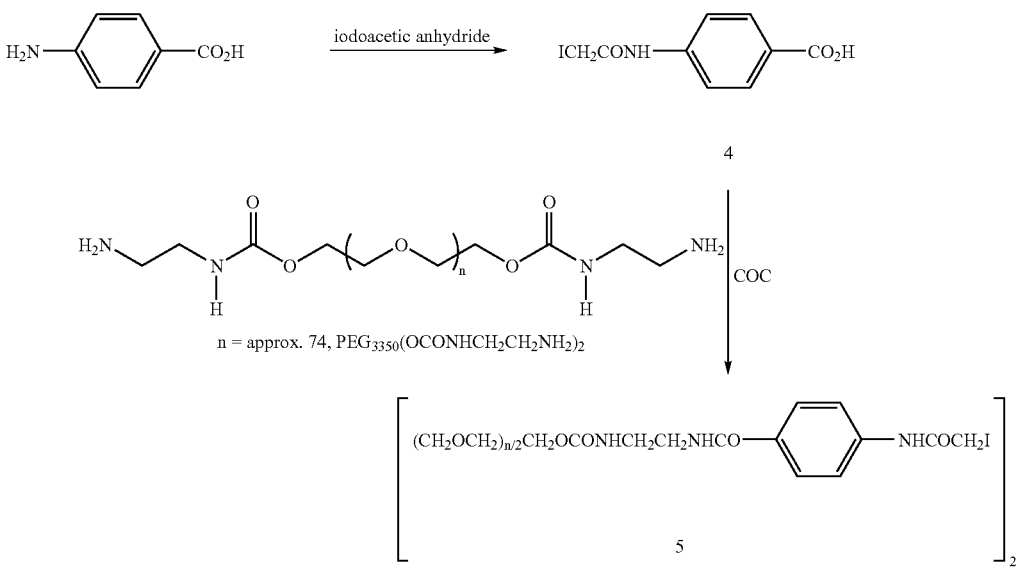

Reaction Schemes 2 n = approx. 74, $PEG_{3350}(OCONHCH_2CH_2NH_2)_2$

Compound 4—[4(iodoacetamido)benzoic acid

This compound was prepared as described by Weltman, J. K., 1983 *Biotechniques* 1:148–152. Briefly, 708 mg (2.0 mmol) of iodoacetic anhydride was added to a solution of 137 mg (1.0 mmol) of para-aminobenzoic acid in 10 mL of dioxane. The mixture was stirred in the dark for 18 hours and partitioned between 25 mL of $H_2O$ and 25 mL of EtOAc. The EtOAc layer was washed with saturated NaCl solution, dried ($MgSO_4$), filtered and concentrated to yield 797 mg of a peach colored solid. Recrystallization from hexanes/EtoAc yielded 221 mg (72%) of 4-(iodoacetamido)benzoic acid as a white solid: mp 220–230°; $^1$H NMR (DMSO) d 3.86 (s, 2H), 7.68 (d, 2H), 7.91 (d, 2H), 10.60 (s, 1H).

Compound 5—[4-(iodoacetamido)benzoyl derivative of α, w-bis-(N-2-aminoethylcarbamolyl)polyethyleneglycol 188 mg (0.909 mmol) of dicyclohexylcarbodiimide was added to a solution of 185 mg (0.606 mmol) of 4-(iodoacetamido)benzoic acid and 406 mg (0.121 mmol) of α, w-bis-(N-2-aminoethylcarbamolyl)polyethyleneglycol (Sigma Chemical Co., St. Louis, Mo., dried by azeotropic distillation with toluene) in 2 mL of THF. The mixture was stirred for 2 hours and then six drops of acetic acid were added. 10 mL of $CH_2Cl_2$ was added and the mixture was kept in a freezer for 30 minutes. The mixture was filtered to remove solids and the filtrate was concentrated to viscous residue. Purification by silica gel chromatography (gradient 99/1 to 96/4 $CH_2Cl_2$/MeOH) provided a solid which was triturated with MeOH to give 292 mg of a cream colored solid: $^1H$ ($CDCl_3$) 3.48 (m, 8H), 3.63 (bd s, $(CH_2CH_2O)_n$, integral too large to integrate), 3.98 (s, 4H), 4.18 (bd m, 4H), 5.91 (bd m, 2H;), 7.48 (bd m, 2H), 7.76 (d, 4H), 7.88 (d, 4H), 9.38 (bd m, 2H): iodoacetyl determination (*European Journal of Biochemistry* 1984, 140, 63–71): Calculated, 0.46 mmol/g; Found, 0.37 mmol/g.

Conjugation of Peptides to Valency Platform Molecule #3 or #5:

All buffers were sparged with helium. The polyethylene glycol (PEG) derivative, #3 or #5 was dissolved in a minimal volume (approximately 20 mg/mL) of 0.05 M $NaHCO_3$ (pH 8.25). Approximately 3 equivalents of peptide were used per iodoacetyl group on the PEG derivative. For para-aminobenzoic acid (PABA)-PEG, containing 2 iodacetyl groups (MW=approximately 4100 g/mole), 6 equivalents of peptide were used for each equivalent of PABA-PEG. For diaminobenzoic acid (DABA)-PEG, containing 4 iodoacetyl groups (MW=approximately 4300 g/mole), 12 equivalents of peptide were used for each equivalent of DABA-PEG. The PEG solution was added to the reduced peptide solution and allowed to react for at least one hour in the dark. The peptide conjugate was purified by preparative HPLC. Before pooling and lyophilization, fractions were checked by electrophoresis using a 15% tricine gel. A description of the compositions of the five peptide conjugates is given in Table 3 and the structures are shown in FIG. 11.

TABLE 3

Conjugates of melittin Peptides and PEG

| Conjugate number | Valence platform | Peptide conjugated | #B cell epitopes/ molecule | Conjugation terminus | T cell activation by peptide or conjugate[1] |
|---|---|---|---|---|---|
| 1 | 5 | 6 | 2 | N | no(pep) |
| 2 | 3 | 6 | 4 | N | no(pep/conj) |
| 3 | 3 | 7 | 4 | C | nd |
| 4 | 3 | 5 | 4 | N | yes(pep) |
| 5 | 3 | 8 | 8[2] | C | nd |

[1]Stimulation of uptake of [$^3$H] thymidine by cultured T cell from melittin-immunized mice; nd = not determined; pep = peptide tested; conj = peptide-PEG conjugate tested.
[2]4 copies of a branched peptide, containing two identical branches each; each branch comprising a B cell epitope

EXAMPLE 6

Studies Using Melittin Peptide Conjugates to Tolerize Mice Primed and Boosted with Melittin Murine Lymph Node Proliferation Assays.

Food and water was provided ad libitum. Balb/c mice were immunized in each hind footpad with 50 μg of melittin molecule in CFA. Popliteal lymph nodes were harvested aseptically seven days later. Lymph nodes were gently dissociated by teasing the cells through a 50 mesh sieve screen. The single cell suspension was washed in RPMI-1640 (Irvine Scientific, Irvine Calif.) containing glutamine, penicillin and streptomycin. $5 \times 10^5$ cells in RPMI medium supplemented with 10% fetal bovine serum (FCS) in quadruplicate wells of round bottom 96-well Corning microtitration plates were cultured with melittin or a melittin peptide at 10, 1.0 or 0.1 μ/mL. Cells in the positive control wells were cultured with murine interleukin 2 (IL-2) at 100 or 50 U/mL, PHA (phytohemagglutinin) at 1 μg/mL. The negative control wells contained lymph node cells in RPM-1640 and 10% FCS. The cells were cultured for 4 days in a 37° C. incubator with 5% $CO_2$. Each well was pulsed with 1 μCi of [$^3$H]thymidine (ICN, Biochemicals, Costa Mesa, Calif.) for an additional 18 hours. Cells were harvested onto a glass fiber filter mat using a semiautomatic cell harvester (Scatron, Sterling, Va.). Incorporation of [$^3$H]thymidine was determined by liquid scintillation. The results were expressed as average counts per minute.

In Vivo Protocols

Balb/c mice were primed intraperitoneally (i.p.) with 4 μg of melittin in CFA. One month later the potential tolerogen or formulation buffer was administered i.p. Three days later all mice received an i.p. injection of 4 μg of melittin in Incomplete Freund's Adjuvant (ICF) (Sigma Chemical Co., St. Louis, Mo.). 100 to 200 μL of blood was collected from the retro-orbital venous plexus 10 days later. Serum samples were assayed for anti-peptide, or anti-melittin, IgG antibodies.

Assay for IgG Anti-Melittin or Anti-Melittin Antibodies

An individual mouse's serum sample was assessed serially for the presence of anti-melittin antibodies by ELISA. Falcon Probind 96-well microtitration plates were precoated with 10 μg/mL melittin or melittin peptide in phosphate buffered saline (PBS), pH 7.2, overnight at 4°. The plates were washed twice with a wash solution containing PBS, 0.02% Tween-20, and 1% gelatin (Norland Products Inc., New Brunswick, N.J.). Plates were blocked with 200 μL PBS containing 5% gelatin for 1 hour at 37°. Serum samples were prepared in a diluent of PBS containing 5% gelatin. Samples were tested at dilutions of 1:100 to 1:1000. After 1 hour of incubation at 37° C., the plates were washed four times. ExtraAvidin peroxidase (Sigma Chemical Co., St. Louis, Mo.) was diluted 1:1000 in PBS containing 5% gelatin. The plates were incubated 30 minutes at 37° C. and then washed five times. Wells were developed with OPD, (ortho phenylene diamine dihydrochloride, Sigma Chemical Co., St. Louis, Mo.) according to the manufacturer's directions, in the dark for 15–30 minutes, and the reaction was stopped with 3 M HCl. The optical density (OD) was determined at 450 nm on a microplate reader (Bio-tek Instruments Winooski, Vt.).

Antibody Forming Cell Assay

Cellulose microtitration plates (Millipore Co., Bedford, Mass.) were prepared as indicated above for the IgG antibody (ELISA) assay. However, at the point in the assay where the serum samples were added to the wells, splenic cells (5×10⁵/well) were added instead of serum, and incubated overnight. The remainder of the ELISA assay was performed as indicated above.

T Cell Epitopes

Figure 6:
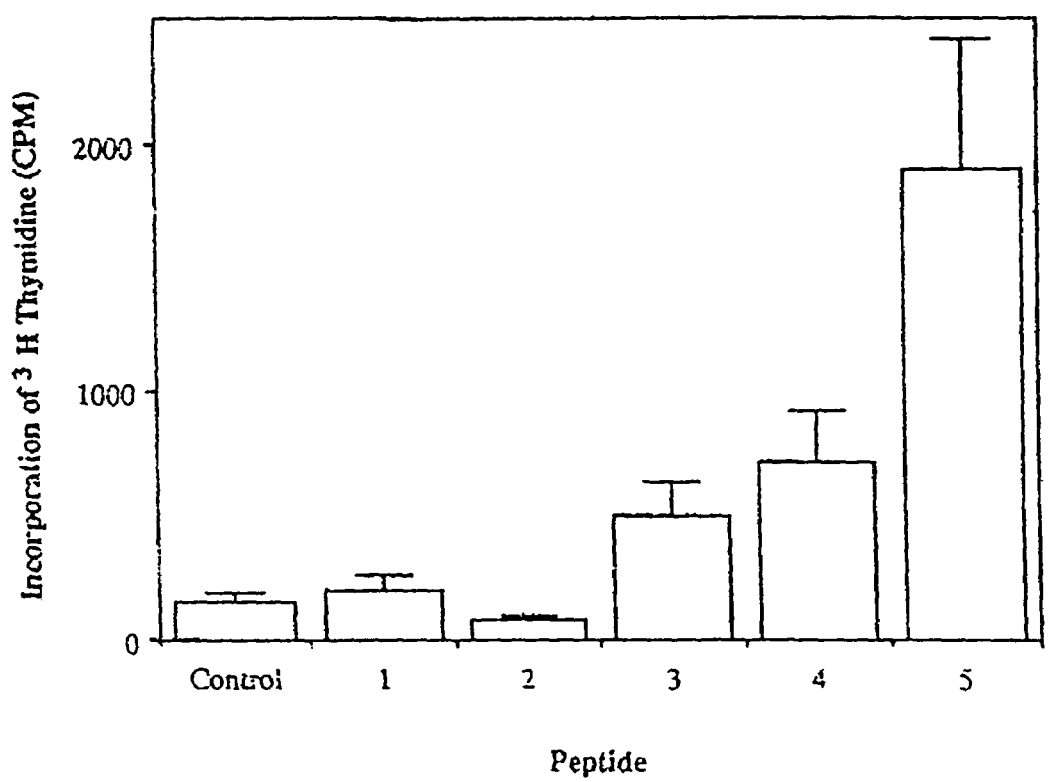
Figure 7:
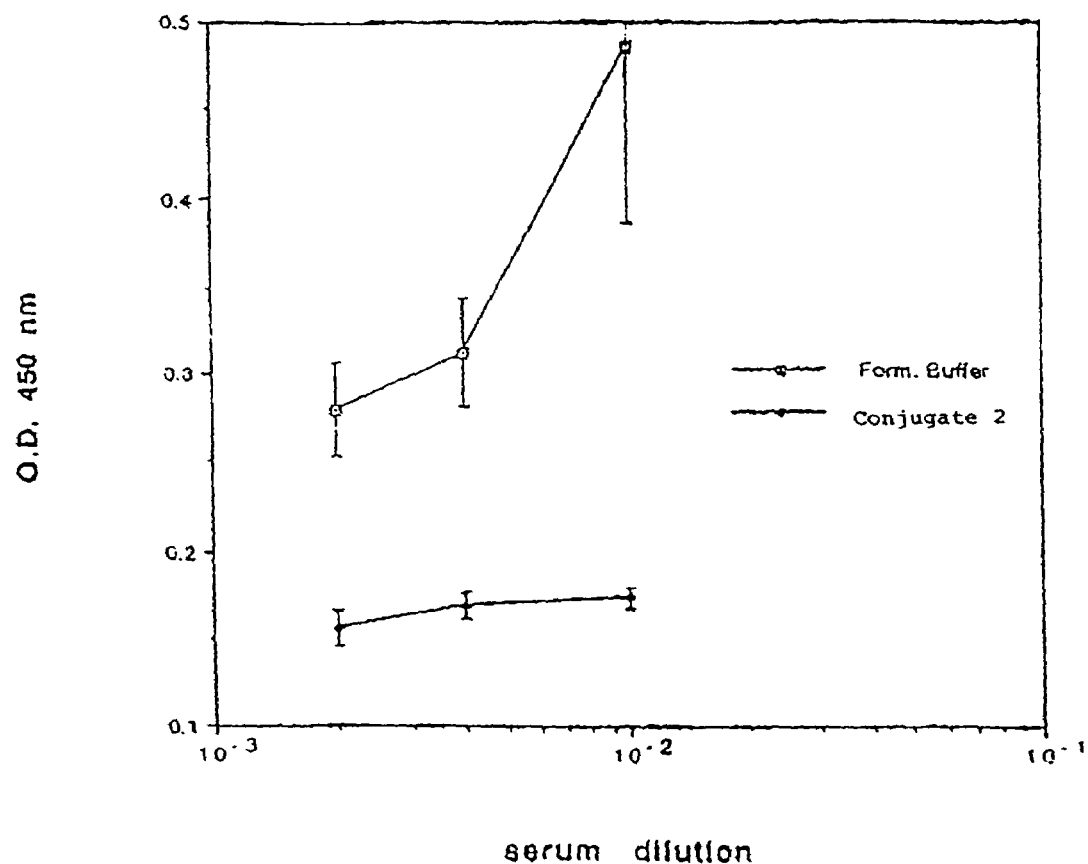
Figure 8:
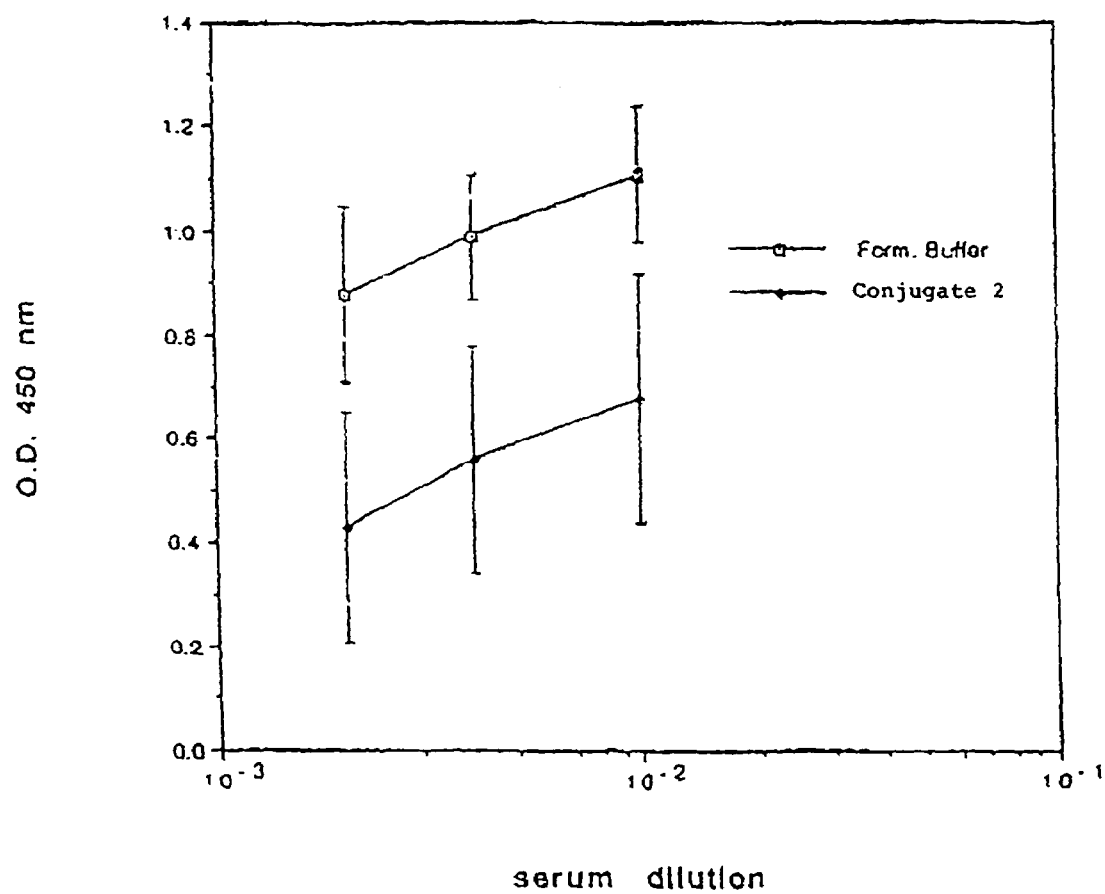
Figure 9:
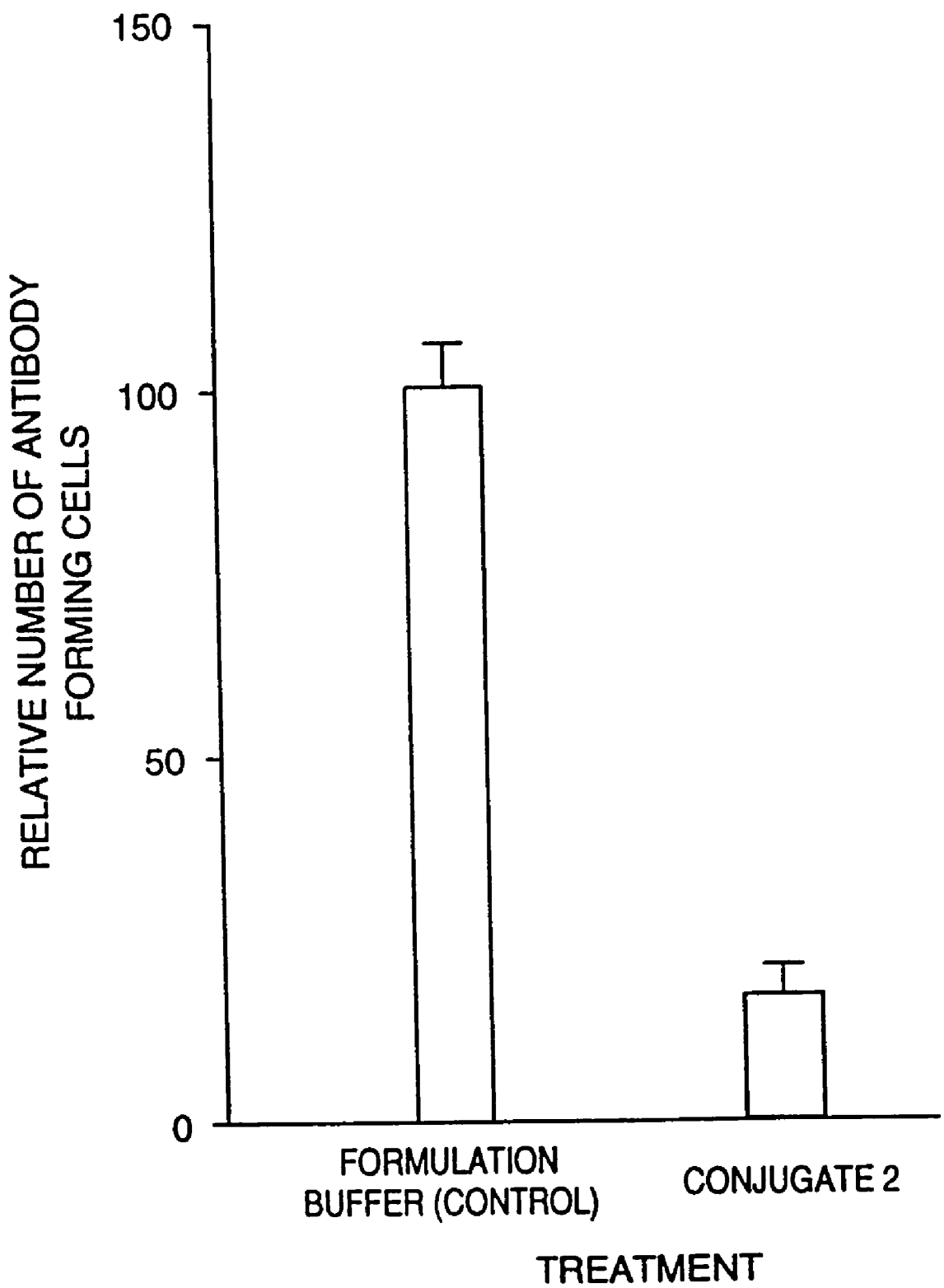
Figure 10:
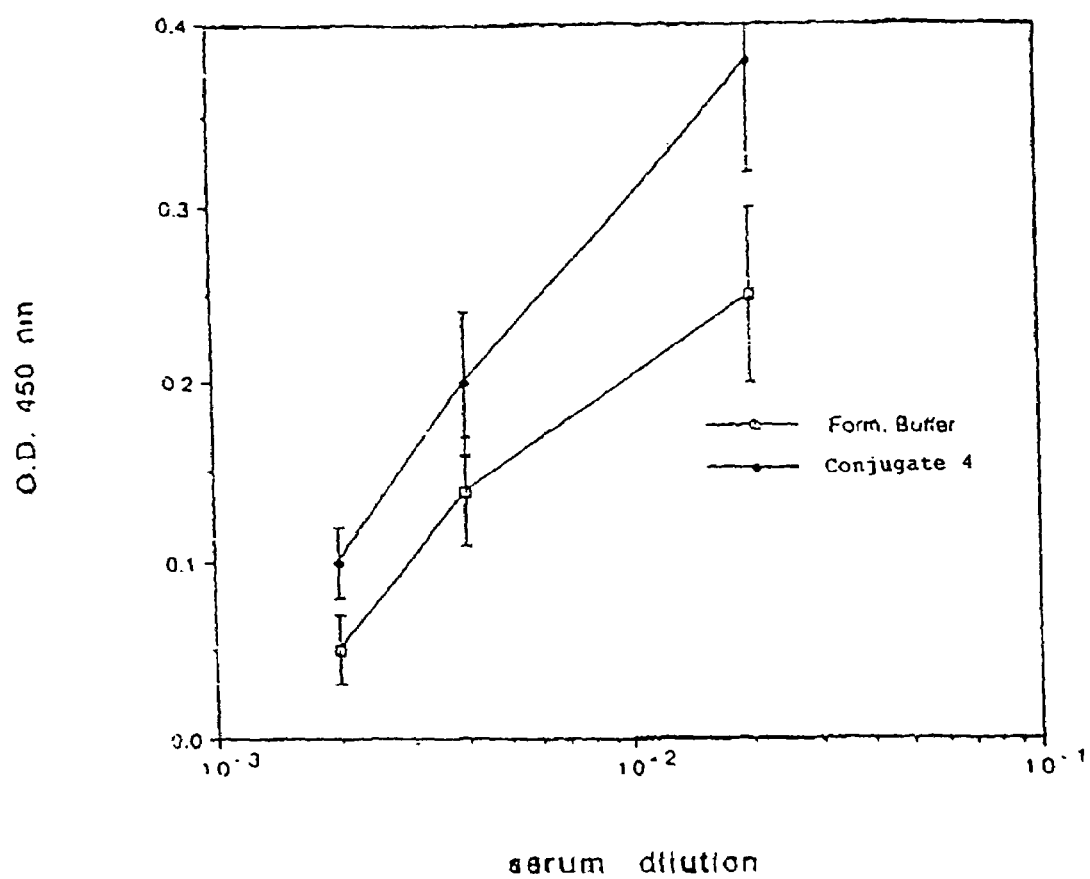

T Cells from mice primed with melittin showed T cell proliferation in response to the whole melittin molecule and to C-terminal melittin peptides 3, 4, and 5 (FIG. 6). However, C-terminal peptides 1 and 2 induced no significant T cell proliferation. Melittin peptides 6 and 5 were conjugated to PEG to make Conjugates 2 and 4, respectively. Like melittin peptide 2, the PEG conjugate of melittin peptide 6 (Conjugate 2) also did not induce significant T cell proliferation. Mice treated with Conjugate 2 (10 mg/kg, 200 μg/mouse), had significantly lower levels of anti-melittin peptide 2 antibodies (FIG. 7) and also lower levels of anti-melittin antibodies (FIG. 8) as compared to the control Balb/c mice treated with formulation buffer. Spleen cells from mice treated with buffer control or Conjugate 2 were assayed for the ability of antibody-forming cells to produce anti-melittin or anti-melittin peptide 2 antibodies as measured in a soluble ELISA assay. As shown in FIG. 9, the levels of anti-melittin peptide 2 antibody forming cells in the Conjugate 2 treatment group were significantly lower than in the control group which was administered formulation buffer. Mice treated with Conjugate 4, a conjugate of peptide 5 (which contains a T cell epitope), failed to reduce the titer of antibodies to peptide 5 in treated mice. Thus, the conjugate containing a T cell epitope was not a tolerogen (FIG. 10). In fact, rather than reduce the response, the levels of anti-peptide antibody may have increased slightly.

EXAMPLE 7

Additional Studies Using Melittin Peptide Conjugates to Tolerize Mice Primed and Boosted with Melittin Female C57BL/6 mice, ages 5 to 8 weeks were purchased from The Jackson Laboratory, Bar Harbor, Me. Animals were maintained and treated accordingly to National Institutes of Health guidelines.

Immunization Protocol

Mice were primed by an i.p. injection containing 5 μg of melittin precipitated on alum and 2×10⁹ B. pertussis as an adjuvant. The mice were boosted with 5 μg of melittin, i.p., in PBS.

pfc Assay

Sheep Red Blood Cells (SRBC) (Colorado Serum Co., Denver, Colo.) were conjugated with melittin-peptide 2 using carbodiimide. Fresh SRBC (less than 2 weeks old) were washed four times with cold saline and one time with mannitol (0.35 M mannitol, 0.01 M NaCl). The SRBC were suspended in mannitol to a concentration of 10% (v/v). 100 μL of mannitol containing 30 μg of melittin peptide #3 were added to 1 mL aliquots of 10% SRBC which were then incubated on ice for 10 minutes. 100 μL of a 100 mg/mL solution of 1-ethyl-3 (3-dimethylaminopropyl)-carbodiimide HCl (EDCI) was then added and incubated on ice for 30 minutes. The SRBC were washed twice with Balanced Salt Solution (BSS) (Irvine Scientific Co, Irvine, Calif.) and resuspended, to 10% (v/v). Lyophilized guinea pig complement (GIBCO, New York, N.Y.) was reconstituted with BSS and then diluted 1:3 with BSS. One mL of the diluted guinea pig complement was added to 3 mL of conjugated SRBC. Rabbit anti-mouse IgG was added to give a final dilution of 1:100 of the rabbit antiserum. This concentration was predetermined to inhibit all IgM pfc while enhancing the maximum number of IgG pfc. An equal volume of this complement/anti-mouse IgG/SRBC suspension was mixed with a cell suspension of mouse spleen cells taken from a single mouse. 50 μL of each mixture was transferred to the chambers of a Cunningham slide (three chambers per slide). The edges were then sealed with paraffin and incubated at 37° C. for one hour. The number of plaques per chamber was counted with the aid of a dissecting microscope. Each spleen suspension was also assayed using non-conjugated SRBC as a control. The number of viable cells, in each spleen cell suspension, was determined. The number of pfc per 10⁶ spleen cells was determined for each chamber and the mean of the triplicates calculated. The number of pfc for non-conjugated SRBC was subtracted from the number of pfc for conjugated-SRBC to determine the number of peptide-specific pfc.

Determining The Optimal Time to Measure pfc

Mice were primed with melittin. Groups (3 mice per group) of primed mice were boosted with melittin on days 2, 4, 6, and 8. On day 10 the mice were sacrificed and their spleens harvested. Cell suspensions were prepared and assayed for the number of peptide specific pfc determined. The optimal number of pfc was obtained 6 days after boosting with melittin.

The Orientation of The Peptide on The PEG Conjugate Does Not Affect The Conjugate's Ability to Induce Tolerance Two different tolerogens were constructed to determine if the orientation of the peptide on the PEG conjugate affects its ability to induce tolerance. Peptide #7 (equivalent to peptide #2 plus C-terminal penultimate insertion of Lys-Cys) was covalently bound to valency platform molecule 3 through its C-terminal end to make melittin Conjugate 3. Groups, (3/group) of mice primed with melittin were treated, i.p., with conjugates or with saline. Five days later all of the mice, including the non-treated control group, were boosted with 5 μp of melittin. Six days later the mice were sacrificed, their spleens were harvested and the number of peptide specific pfc determined. As illustrated in Table 4, both orientations were effective in reducing the number of peptide-specific pfc/10⁶ spleen cells in mice primed and boosted with the parent protein melittin.

TABLE 4

Orientation of the peptide on the PEG conjugate does not affect the conjugates' ability to induce tolerance

| Melittin Conjugate# | μg/mouse | Peptide specific pfc per 10⁶ spleen cells (Mean and S.D.) | % Reduction |
|---|---|---|---|
| 3 | 1000 μg | 386 (85) | 86.8% |
| " | 500 μg | 489 (one mouse) | 83.3% |
| " | 250 μg | 957 (298) | 67.3% |
| 2 | 1000 μg | 546 (160) | 81.3% |
| " | 500 μg | 866.6 (235) | 70.4% |
| " | 250 μg | 1280 (one mouse) | 56.2% |
| None | None | 2924 (164) | — |

The Number of Peptides Per PEG Conjugate Affects The Conjugate's Ability to Induce Tolerance Three different conjugates, each with a different number, of peptides per PEG conjugate, were constructed to determine if the ratio of peptides to PEG molecule was important. Conjugate 1 had only two peptides per PEG conjugate. Another had four peptides per PEG conjugate (Conjugate 2). The third had four, branched peptides (8 B cell epitopes) per PEG conjugate (Conjugate 5). Groups (3/group) of mice primed with melittin were treated, i.p., with the different conjugates or with saline. Five days later all of the mice, including the non-treated control group, were boosted with 5 µg of melittin. Six days later, the mice were sacrificed, their spleens were harvested and the number of peptide-specific pfc determined. As shown in Table 5, Conjugate 1, containing two peptides per PEG molecule, was ineffective in reducing the number of peptide-specific pfc/$10^6$ spleen cells in mice primed and boosted with the parent protein melittin. The results show that both melittin conjugates 2 and 5 were effective as tolerogens; however, conjugate 5 which contained 8 epitopes (4 branched peptides) was effective at a lower dose than conjugate 2, which contained four unbranched peptides per valency platform molecule.

TABLE 5

The number of peptides per PEG conjugate affects the conjugates' ability to induce tolerance

| Treatment Molecule | Dose µg/mouse (nMoles) | Peptide specific indirect IgG pfc(SD) | % Reduction |
| --- | --- | --- | --- |
| No treatment | | 1159(280) | std |
| Conjugate 1 | 1000(217) | 1290(98) | −11% |
| | 250(54) | 1350(206) | −16% |
| Conjugate 2 | 500(80) | 585(125) | 49.5% |
| | 250(40) | 1001(176) | 14% |
| Conjugate 5 | 500(53) | 630(325) | 45.6% |
| | 250(26.5) | 443(105) | 61.8% |
| | 125(13.25) | 583(69) | 49.7% |

Modifications of the above-described modes for carrying out the invention that are obvious to those of ordinary skill in the fields of immunology, chemistry, medicine and related arts are intended to be within the scope of the following claims.

The invention claimed is:

1. A method of identifying a polypeptide analog of a T cell-dependent immunogen implicated in an antibody-mediated pathology comprising the steps of:

(a) screening a panel or library of candidate polypeptides for the presence of one or more B cell epitope(s) that specifically binds to antibodies to which the immunogen binds specifically;

(b) screening said candidate polypeptides identified in step (a) for candidate polypeptides lacking T cell epitope(s); and (c) selecting a polypeptide analog from said candidate polypeptides that bind to the antibodies of step (a), but that do not contain T cell epitope(s) as determined by step (b).

2. The method of claim 1, wherein the immunogen is an external immunogen.

3. The method of claim 2, wherein the external immunogen is a biological drug, allergen or a D immunogen associated with Rh hemolytic disease.

4. The method of claim 1, wherein the immunogen is a self-immunogen.

5. The method of claim 4, wherein the self-immunogen is that associated with thyroiditis, diabetes, stroke, male infertility, myasthenia gravis, or rheumatic fever.

6. A method of making a polypeptide analog of a T cell-dependent immunogen implicated in an antibody-mediated pathology comprising the step of removing T cell epitope(s) from a polypeptide comprising an epitope that binds specifically to antibodies to which the immunogen binds specifically.

7. The method of claim 6, wherein the immunogen is an external immunogen.

8. The method of claim 7 wherein the external immunogen is a biological drug, allergen or a D immunogen associated with Rh hemolytic disease.

9. The method of claim 6, wherein the immunogen is a self-immunogen.

10. The method of claim 9, wherein the self-immunogen is that associated with thyroiditis, diabetes, stroke, male infertility, myasthenia gravis, or rheumatic fever.

11. The method of claim 6, wherein the T cell epitope(s) is removed by altering the T cell epitope(s).

12. The method of claim 6, wherein the T cell epitope(s) is removed by deleting the T cell epitope(s).

13. A method of making a polypeptide analog of a T cell-dependent immunogen implicated in an antibody-mediated pathology comprising the steps of:

(a) synthesizing the polypeptide analog, whereby the polypeptide analog comprises an epitope that binds specifically to antibodies to which the immunogen binds specifically, wherein the analog lacks T cell epitopes capable of activating T cells in an individual; and (b) purifying the analog.

14. The method of claim 13, wherein the immunogen is an external immunogen.

15. The method of claim 14, wherein the external immunogen is a biological drug, allergen or a D immunogen associated with Rh hemolytic disease.

16. The method of claim 13, wherein the immunogen is a self-immunogen.

17. The method of claim 16, wherein the self-immunogen is that associated with thyroiditis, diabetes, stroke, male infertility, myasthenia gravis, or rheumatic fever.

* * * * *

SEQUENCE LISTING

<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Arg Ser Lys Ser Lys Ser Lys Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic construct

<400> SEQUENCE: 2

Ile Lys Arg Lys Arg Gln Gln Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Trp Ile Lys Arg Lys Arg Gln Gln Gly
1               5

<210> SEQ ID NO 4
<211> LENGTH: 10
<212> TYPE: PRT
<213> ORGANISM: Artificial Sequence
<220> FEATURE:

<223> OTHER INFORMATION: Synthetic construct

<400> SEQUENCE: 4

Ser Trp Ile Lys Arg Lys Arg Gln Gln Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic construct

<400> SEQUENCE: 5

Ile Ser Trp Ile Lys Arg Lys Arg Gln Gln Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic construct

<400> SEQUENCE: 6

Cys Ile Ser Trp Ile Lys Arg Lys Arg Gln Gln Gly
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa = This position is H2N
<220> FEATURE:
<221> NAME/KEY: VARIANT
<222> LOCATION: 14
<223> OTHER INFORMATION: Xaa = This position is CO2H

<400> SEQUENCE: 7

Xaa Cys Ile Ser Trp Ile Lys Arg Lys Arg Gln Gln Gly Xaa
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa = This position is H2N
<220> FEATURE:
<221> NAME/KEY: VARIANT
<222> LOCATION: 12
<223> OTHER INFORMATION: Xaa = This position is CO2H

<400> SEQUENCE: 8

Xaa Cys Trp Ile Lys Arg Lys Arg Gln Gln Gly Xaa
1               5                   10

<210> SEQ ID NO 9
<211> LENGTH: 13
<212> TYPE: PRT

```
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa = This position is H2N
<220> FEATURE:
<221> NAME/KEY: VARIANT
<222> LOCATION: 13
<223> OTHER INFORMATION: Xaa = This position is CO2H

<400> SEQUENCE: 9

Xaa Trp Ile Lys Arg Lys Arg Gln Gln Lys Cys Gly Xaa
 1               5                  10

<210> SEQ ID NO 10
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa =This position is H2N
<220> FEATURE:
<221> NAME/KEY: VARIANT
<222> LOCATION: 21
<223> OTHER INFORMATION: Xaa= This position if CO2H

<400> SEQUENCE: 10

Xaa Trp Ile Lys Arg Lys Arg Gln Gln Trp Ile Lys Arg Lys Arg Gln
 1               5                  10                  15

Gln Lys Cys Gly Xaa
            20

<210> SEQ ID NO 11
<211> LENGTH: 28
<212> TYPE: PRT
<213> ORGANISM: Melittin from bee venom
<220> FEATURE:
<221> NAME/KEY: VARIANT
<222> LOCATION: 1
<223> OTHER INFORMATION: Xaa = This position is H2N
<220> FEATURE:
<221> NAME/KEY: VARIANT
<222> LOCATION: 28
<223> OTHER INFORMATION: Xaa = This position is CO2H

<400> SEQUENCE: 11

Xaa Gly Ile Gly Ala Val Leu Lys Val Leu Thr Thr Gly Leu Pro Ala
 1               5                  10                  15

Leu Ile Ser Trp Ile Lys Arg Lys Arg Gln Gln Xaa
            20                  25
```